(12) United States Patent
Wen et al.

(10) Patent No.: US 9,605,268 B2
(45) Date of Patent: Mar. 28, 2017

(54) METHOD FOR INTRODUCING AN EXOGENOUS DNA BY OVERCOMING THE RESTRICTION MODIFICATION BARRIER OF A TARGET BACTERIUM

(71) Applicant: Institute of Microbiology, Chinese Academy of Sciences, Beijing (CN)

(72) Inventors: Tingyi Wen, Beijing (CN); Guoqiang Zhang, Beijing (CN); Aihua Deng, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 0 days.

(21) Appl. No.: 14/385,940

(22) PCT Filed: Feb. 21, 2013

(86) PCT No.: PCT/CN2013/071730
§ 371 (c)(1),
(2) Date: Sep. 17, 2014

(87) PCT Pub. No.: WO2013/139193
PCT Pub. Date: Sep. 26, 2013

(65) Prior Publication Data
US 2015/0050740 A1 Feb. 19, 2015

(30) Foreign Application Priority Data

Mar. 23, 2012 (CN) .......................... 2012 1 0080124

(51) Int. Cl.

| | |
|---|---|
| *C12N 1/20* | (2006.01) |
| *C12N 15/70* | (2006.01) |
| *C12R 1/19* | (2006.01) |
| *C12N 9/10* | (2006.01) |
| *C12N 15/74* | (2006.01) |
| *C12N 15/75* | (2006.01) |

(52) U.S. Cl.
CPC .............. *C12N 15/70* (2013.01); *C12N 1/20* (2013.01); *C12N 9/1007* (2013.01); *C12N 15/74* (2013.01); *C12N 15/75* (2013.01); *C12R 1/19* (2013.01); *C12Y 201/01037* (2013.01)

(58) Field of Classification Search
None
See application file for complete search history.

(56) References Cited

FOREIGN PATENT DOCUMENTS

| CN | 102618476 | 8/2012 |
| WO | WO-01/85966 A2 | 11/2001 |

OTHER PUBLICATIONS

Kumar et al., Chapter 4, Epigenetics: Development and Disease, 2013.*
Mestrovic, DNA Methylation in Bacteria, News Medical, downloaded from: http://www.news-medical.net/life-sciences/DNA-Methylation-in-Bacteria.aspx.*
Yasui, et al., "Improvement of bacterial transformation efficiency using plasmid artificial modification". Nucleic Acids Research, Nov. 12, 2008, vol. 37, No. 1, pp. 1-7.
Zhou, "Non-restricting and methylation deficient *Escherichia coli* strains for bacterial secondary metabolism research", Chinese Master's Theses Full-test Database Engineering Scinence and Technology I , Jan. 15, 2012 (Jan. 15, 2012), vol. 2012, No. 01, pp. 27-32, 39-40.
Zhang, et al., "A Mimicking-of-DNA-Methylation-Patterns Pipeline for Overcoming the Restriction Barrier of Bacteria", PLos Genet. Sep. 27, 2012, vol. 8, No. 9, pp. 1-15.
Hirokazu, "Host-Mimicking Strategies in DNA Methylation for Improved Bacterial Transfirmation. Methylation—From DNA, RNA and Histones to Diseases and Treatment", Nov. 28, 2012, pp. 219-316, ISBN 978-953-51-0881-8.
Hirokazu, et al., "Inprovement of Transformation Efficiency by Strategic Cirecumvention of Restriction Barriers in Streptomyces griseus", J. Microbiol. Biotechol. May 14, 2011, vol. 21, No. 7, pp. 675-678.
Roberts, "A database for DNA resreiction and modification: enzymes, genes and geomes", Nucleic Acids Research. Oct. 21, 2009, vol. 38, pp. D234-D236.
Guzman, et al., "Tight Regulation, Modulation, and High-Level Expression by Vectors Containing the Arabinose $P_{BAD}$ Promoter", Journal of Bacteriology, 1995 177:4121-30.
Zacchi, et al., "Mds3 Regulates Morphogenesis in *Candida albicans* through the TOR Pathway", Molecular and Cellular Biology, 2010, 30: 3695-3710.
Marinus et al "Biological Function for 6-Methyladenine Residues in the DNA of *Escherichia coli* K12" Journal of Molecular Biology vol. 85, pp. 309-322. 1974.
Office Action issued for Japanese Application No. 2015-502066.
Kessler et al "Recognition Sequences of Restriction Endonucleases and Methylases—A Review" Gene vol. 33, pp. 1-102, 1985.
Palmer et al "The dam and dcm Strains of *Escherichia coli*—A Review" Gene vol. 143, pp. 1-12, 1994.
Xu, et al., "A novel host-specific restriction system associated with DNA backbone S-modification in *Salmonella*", Nucleic Acids Research, Jul. 12, 2010, 38, 7133-7141.
Donahue, et al., "Overcoming the restriction barrier to plasmid transformation of *Helicobacter pylori*", Molecular Microbiology, May 24, 2000, 37, 1066-1074.
Groot, et al., "Enhanced Transformation Efficiency of Recalcutrant *Bacillus cereus* and *Bacillus weihenstephanensis* Isolates upon In Vitro Methylation of Plasmid DNA", Applied and Environmental Microbiology, Dec. 2008, 74, 7817-7820.
Van Der Rest, et al., "A heat shock following electroporation induces highly efficient transformation of *Corynebacterium glutamicum* with xenogenic plasmid DNA", Microbial Biotechnology, Jun. 11, 1999, 52, 541-545.

(Continued)

*Primary Examiner* — Anne Gussow
*Assistant Examiner* — Mindy G Brown
(74) *Attorney, Agent, or Firm* — Cesari and McKenna LLP

(57) ABSTRACT

Disclosed is a method for introducing an exogenous DNA by overcoming the restriction modification barrier of the target bacterium. The method includes the steps of 1) co-expressing all DNA-methyltransferase-encoding genes in the genome of the target bacterium in *E. coli* in which the restriction modification system thereof has been deleted to obtain a recombinant bacterium A, 2) introducing an exogenous DNA molecule into the recombinant bacterium A for in vivo modification so as to obtain a methylation-modified exogenous DNA molecule, and 3) introducing the methylation-modified exogenous DNA molecule into the target bacterium.

10 Claims, 6 Drawing Sheets

(56) References Cited

OTHER PUBLICATIONS

Dong, et al.,"Engineering *Clostridium* Strain to Accept Unmethylated DNA", PLoS One, Feb. 9, 2010, 5, e9038.

Veiga, et al., "Inactivation of the SauI Type I Restriction-Modification System is not Sufficient to Generate *Staphylococcus aureus* Strains Capable of Efficiently Accepting Foreign DNA", Applied and Environmental Microbiology, May 2009, 75, 3034-3038.

Gietz, et al., "Transformation of Yeast by Lithium Acetate/Single-Stranded Carrier DNA/Polyethylene Glycol Method", Methods in Enzymology, 2002, 350, 87-96.

Robzyk, et al., "A simple and highly efficient procedure for rescuing autonomous plasmids from yeast", Nucleic Acids Research, May 6, 1992, 20, 3790.

Zhang, et al., "Complete Genome Sequence of *Bacillus amyloliquefaciens* TA208, a Strain for Industrial Production of Guanosine and Ribavirin", Journal of Bacteriology, Apr. 22, 2011, 193(12): 3142-3143.

Zhang, et al., "Enhancing electro-transformation competency of recalcitrant *Bacillus amyloliquefaciens* by combining cell-wall weakening and cell-membrane fluidity disturbing", Analytical Biochemistry, Feb. 1, 2011, 409, 130-137.

Fabret, et al., "A new mutation delivery system for genome-scale approaches in *Bacillus subtilis*", Molecular Microbiology, Jul. 4, 2002, 46, 25-36.

Kovach, et al., "Four new derivatives of the broad-host-range cloning vector pBBR1MCS, carrying different antibiotic-resistance cassettes", Gene, Aug. 21, 1995, 166(1): 175-176.

Carsiotis, et al., "Genetic engineering of enhanced microbial nitrification", US Environmental Protection Agency, Risk Reduction Engineering Laboratory. Jun. 1989.

\* cited by examiner

METHOD FOR INTRODUCING AN EXOGENOUS DNA BY OVERCOMING THE RESTRICTION MODIFICATION BARRIER OF A TARGET BACTERIUM

CROSS REFERENCE TO RELATED APPLICATIONS

This application is the National Stage of International Application No. PCT/CN2013/071730, filed on Feb. 21, 2013, which claims the benefit of Chinese Application No. 201210080124.6, filed on Mar. 23, 2012. The contents of both applications are hereby incorporated by reference in their entirety.

TECHNICAL FIELD

The present invention relates to the biotechnical field, and especially relates to a method for introducing an exogenous DNA by overcoming the restriction modification barrier of a target bacterium.

BACKGROUND ART

The bacterial restriction modification system consists of restriction endonucleases (restriction enzymes) and DNA methyltransferases, and the former are able to specifically recognize and cleave DNA while the latter are able to add a methyl modification to a base of DNA to prevent the cleavage of DNA by restriction enzymes. The Restriction modification system is able to selectively degrade exogenous DNA invading into bacteria to enable self-protection of bacteria. Restriction modification systems are divided into four major types, according to their subunit constitutions, cleavage sites, sequence specificities, and co-factor characteristics. Subunits of restriction enzymes of the restriction modification systems type I, type II, and type III are able to recognize and cleave non-methylated DNA. However, if DNA is first recognized and modified by the subunit of the methyltransferase, cleavage cannot be achieved by the restriction enzyme. The restriction modification system type IV consists of only the restriction enzymes and does not contain the methyltransferases. It recognizes and cleaves DNA having an exogenous methylation pattern, and thus is a methylation-dependent restriction enzyme. Additionally, a recent study indicates that phosphorothioation-modification-enzymes for DNA backbones and corresponding restriction enzymes thereof are a new type of restriction modification systems (Nucleic Acids Research, 38, 7133-7141). Such a complex modification-cleavage mode considerably protects the safety of bacteria's own DNA and is used as a main means of bacteria for effectively preventing invasion of exogenous DNA released by bacteriophages and dead bacteria in the environment. Meanwhile, this also becomes the main barrier for introducing an exogenous DNA into bacteria and enabling genetic manipulation by using molecular biological methods. The genetic manipulation of bacteria having multiple restriction modification systems is especially difficult.

To date, investigators have invented two types of techniques for overcoming the restriction modification barriers. The first strategy is modifying exogenous DNAs, including in vitro modification and in vivo modification of *E. coli*. For example, in vitro modification of exogenous DNAs using crude protein extract (containing DNA methyltransferase) of the target bacterium enables transformation of *Helicobacter pylori*, *Bacillus cereus*, and *Bacillus weihenstephanensis* (Molecular Microbiology, 37, 1066-1074, Applied and Environmental Microbiology, 74, 7817-7820); or cloning and expression of DNA methyltransferase of the target bacterium in *E. coli* and in vivo modification of exogenous plasmid DNAs, for example, cloning and expression of two DNA methyltransferases of *Bifidobacterium adolescentis* in *E. coli* TOP10 and modification of shuttle plasmids, enables genetic transformation of *Bifidobacterium adolescentis* (Nucleic Acids Research, 37, e3). The second type, i.e., a method for inactivating restriction modification systems, includes inactivation by physical means and gene knockout. By transitorily inactivating restriction enzymes of the target bacterium using heating after transformation, the transformation efficiency of exogenous plasmids for *Corynebacterium glutamicum* is increased to $10^8$ CFU/µg DNA (Microbial Biotechnology, 52, 541-545); after gene CAC1502 is knocked out, *Clostridium acetobutylicum* can be allowed to accept unmethylated plasmid DNA (PLoS ONE, 5, e9038); and however, there is also a report indicating that knockout of SauI restriction endonuclease is not sufficient to allow *Staphylococcus aureus* to accept exogenous DNAs (Applied and Environmental Microbiology, 75, 3034-3038).

Although the techniques described above may increase transformation efficiency of exogenous DNAs for target bacterium to some extent, there are still the following problems and deficiencies: Although some solutions are able to perform in vitro modification on exogenous DNA molecules using DNA methyltransferases of the target bacterium, in vitro modification efficiency using the crude protein extract is low, and a part of plasmids would be also degraded at the same time of modification; the solution of in vivo modification has not eliminated methylation of exogenous DNA molecules by *E. coli*'s own DNA methyltransferases, and such DNAs having an *E. coli* methylation pattern are prone to activate the restriction system type III of the target bacterium. Restriction enzymes of a number of bacteria are not heat-sensitive and cannot be transitorily inactivated by heating; if a bacterium contains multiple restriction modification systems, a lot of time and effort are needed to knockout restriction enzyme genes one by one, and meanwhile, knockout of restriction enzymes also causes the target bacterium to be infected by bacteriophages, which is extremely adverse to the construction of strains for industrial microbial fermentation. The techniques have poor generality and may be only applicable to one or a few types of bacteria.

SUMMARY OF THE INVENTION

An object of the present invention is to provide a method for introducing an exogenous DNA molecule into a target bacterium.

The method provided in the present invention comprises the steps of 1) co-expressing all DNA-methyltransferase-encoding genes in the genome of a target bacterium in *E. coli* in which the restriction modification system thereof has been deleted to obtain a recombinant bacterium A;

2) introducing an exogenous plasmid DNA molecule into said recombinant bacterium A for in vivo modification so as to obtain a methylation-modified exogenous DNA plasmid molecule;

3) introducing said methylation-modified exogenous plasmid DNA molecule into said target bacterium.

In the method described above, in step 1), said co-expression of all DNA-methyltransferase-encoding genes in the genome of the target bacterium in *E. coli* in which the restriction modification system thereof has been deleted, is introduction, via a recombinant vector, of all DNA-methyltransferase-encoding genes in the genome of the target bacterium into said E. coli in which the restriction modification system thereof has been deleted; and step 2) comprises the steps of A) introducing said exogenous plasmid DNA molecule into said recombinant bacterium A to obtain a recombinant bacterium B;

B) inducing and culturing said recombinant bacterium B to obtain an induced recombinant bacterium B;

C) extracting the plasmid DNA of said induced recombinant bacterium B to obtain a methylation-modified exogenous plasmid DNA molecule.

In the method described above, in step 1) said recombinant vector is one which coexpresses all DNA methyltransferases obtained by inserting all DNA-methyltransferase-encoding genes into an expression plasmid; and each DNA-methyltransferase-encoding gene in the recombinant vector described above can use respective promoters or share one promoter (constituting an operon structure).

In B) of step 2), said inducing and culturing comprises a temperature induction or induction using an inducing agent such as arabinose, IPTG, xylose, or rhamnose.

In the method described above, in 13) of step 2), said inducing and culturing comprises culturing the recombinant bacterium B under inducing conditions;

the optimal inducing conditions are that said recombinant bacterium B is inducing and culturing in a liquid culture medium containing arabinose at a final concentration of 0.2% by mass;

the temperature for said inducing and culturing is 25° C.-37° C. and the time for said inducing and culturing is 3-24 hours; and the temperature for said inducing and culturing is preferably 30° C. and the time for said inducing and culturing is preferably 12 hours.

In the method described above, said target bacterium is an Eubacterium or Archaebacterium containing a restriction modification systems, and said Eubacterium or Archaebacterium containing restriction modification systems can be, but is not limited to, Bacillus amyloliquefaciens TA208, Bacillus cereus ATCC 10987, or Nitrobacter hamburgensis X14;

said E. coli in which the restriction modification system thereof has been deleted can be, but is not limited to, Escherichia coli EC135 CGMCC NO. 5925; the genotype of the restriction modification system thereof is mcrA Δ (mrr-hsdRMS-mcrBC) Δdcm::FRT Δdam::FRT.

In the method described above, said exogenous DNA molecule can be, but is not limited to, pAD123, pAD43-25, pMK3, pMK4, pHCMC02, pHCMC04, pDG148StuI, pWYE748, or pBBR1-MCS5-$P_{Nham\_3450}$-GFP.

In the method described above, all DNA-methyltransferase-encoding genes in said Bacillus amyloliquefaciens TA208 are BAMTA20806525, BAMTA208_6715, BAMTA208_19835 and BAMTA208_16660; and nucleotide sequences of said BAMTA208_06525, BAMTA208_6715, BAMTA208_19835 and BAMTA208_16660 are, in this order, SEQ ID NO: 2, SEQ ID NO: 3, SEQ ID NO: 4, and SEQ ID NO: 5 in the sequence listing;

all DNA-methyltransferase-encoding genes in said Bacillus cereus ATCC 10987 are BCE_0393, BCE_4605, BCE_5606, BCE_5607, BCE_0365, and BCE_0392; and nucleotide sequences of said BCE_0393, BCE_4605, BCE_5606, BCE_5607, BCE_0365 and BCE_0392 are, in this order, SEQ ID NO: 6, SEQ ID NO: 7, SEQ ID NO: 8, SEQ ID NO: 9, SEQ ID NO: 10, and SEQ ID NO: 11 in the sequence listing; and all DNA-methyltransferase-encoding genes in said Nitrobacter hamburgensis X14 are Nham_0569, Nham_0582, Nham_0803, and Nham_3225; and nucleotide sequences of said Nham_0569, Nham_0582, Nham_0803, and Nham_3225 are, in this order, SEQ ID NO: 12, SEQ ID NO: 13, SEQ ID NO: 14, and SEQ ID NO: 15 in the sequence listing.

Before the steps described above, a step of determining all DNA-methyltransferase-encoding genes in the genome of the target bacterium may be included:

(a) predicting genes encoding DNA methyltransferases in target bacterium by homologous sequence alignment and the like;

(b) introducing each gene encoding DNA methyltransferases, as predicted, to an inducible expression vector respectively, transferring it into E. coli with no restriction modification system, and then inducing and culturing it respectively;

(C) preparing genome DNAs (including chromosomal DNAs and the expression vector) of the aforementioned E. coli into which the expression vector is transferred, and detecting whether DNAs have been methylation-modified, wherein if it is determined that DNAs have been methylation-modified, it is proven that the predicted DNA methyltransferases do have the function of DNA methylation modification and the proteins thereof have activity in E. coli. Detection methods include high-performance liquid chromatography and DNA dot hybridization method.

The DNA methyltransferases described above include methyltransferases type I, type II, and type III, and a DNA methyltransferase type I should include a methyl transfer subunit and a DNA recognition subunit.

Wherein, although said inducible expression vector may be a low-copy vector or may be a high-copy vector, it should be compatible with shuttle/integration plasmids for transforming target bacterium. Promoters for methyltransferases may be promoters of themselves, or may be inducible promoters of E. coli, and include, but is not limited to, arabinose-inducible promoter, IPTG-inducible promoter, and rhamnose-inducible promoter. The induction temperature for a methyltransferase is 8° C.-43° C.

Said E. coli with no restriction modification system is an E. coli wherein all known restriction enzymes and DNA methyltransferases including, but is not limited to, Dam, Dcm, EcoKI, Mrr, McrA, and Mrr have been deleted.

Another object of the present invention is to provide an E. coli EC135.

The E. coli provided in the invention has a deposit accession number of CGMCC No. 5925.

The strain EC135 was deposited under the terms of the Budapest Treaty on the International Recognition of the Deposit of Microorganisms for the Purpose of Patent Procedure in China General Microbiological Culture Collection Center (simply referred to as CGMCC; Address: No. 1 Beichen West Road, Chaoyang District, Beijing, Institute of Microbiology Chinese Academy of Sciences, Postal Code 100101) on Mar. 21, 2012, with a Deposit No. of CGMCC No. 5925, and the category thereof is designated as Escherichia coli.

The methods for transforming target bacterium vary with different target bacterium selected, and include, but is not limited to, a chemical transformation method, conjugative transfer, an electrical transformation method, and a protoplast transformation method.

The experiments of the invention have demonstrated that the invention has the following advantages compared to prior methods for enabling genetic manipulation by overcoming the restriction modification barrier of bacteria.

1. By using a strain of *E. coli* whose restriction modification system has been completely deleted as a host, on one hand, the activation effect of the *E. coli* modification pattern (Dam, Dcm, and EcoKI) on the restriction modification system type IV of the target bacterium is overcome, and on the other hand, deletions of Mrr, McrA and, McrBC of *E. coli* is favorable to the expression and cloning of DNA methyltransferases of the target bacterium;

2. By co-expressing all DNA methyltransferases of the target bacterium, precise simulation of the DNA methylation pattern of the target bacterium has been achieved;

3. What is used is in vivo DNA methylation modification in *E. coli*, which is performed in the process of culturing bacteria without additional in vitro reactions and without methylation reaction substrates added, and is convenient and fast;

4. In the invention, *Saccharomyces cerevisiae* may be used to assemble several methyltransferase genes, and the construction of a co-expression plasmid may be achieved within one week, accelerating the process in which the target bacterium overcomes the restriction modification barrier;

5. The restriction modification system of the transformants of the target bacterium obtained using this method is the same as that of original strains. This method will not damage original restriction modification system of the target bacterium;

6. The invention has good generality, and has been successfully applied to genetic manipulations of two strains of *Bacillus amyloliquefaciens* and a strain of Gram-negative chemoautotrophic bacteria, and is expected to be expanded to more genera and species.

The invention is significant to the construction of the genetic manipulation system of intractable bacteria having multiple restriction modification systems.

SPECIFIC EMBODIMENTS

The following examples facilitate better understanding of the invention, instead of limiting the invention. The experimental methods described below are all conventional methods, unless specified otherwise. The test materials used in the examples described below are all commercially available from conventional biochemical reagent stores, unless specified otherwise. The quantitative tests in the examples below are all set with triplicate experiments, and results show average values.

Example 1

Construction of *E. coli* EC135 Whose Restriction Modification System has been Completely Deleted

*E. coli* TOP10 (Catalog No. CD101, Beijing TransGen Biotech Co., Ltd.) was used as the an original strain and, in the following order, gene dcm (Dcm methylase encoding gene) thereof was knocked out; chromosomal recA gene was mutated to wild type, and gene dam (Dam methylase encoding gene) was knocked out, respectively, to obtain *E. coli* EC135. Details were as follows.

Competent cells of the strain TOP10 was prepared; a plasmid pKD46 (No. 7739, purchased from Coli Genetic Stock Center, U.S., simply referred to as CGSC below) was transformed into the strain TOP10, and ampicillin-resistant transformants were screened at 30° C. to obtain TOP10/pKD46.

The chloramphenicol resistance gene was amplified with primers WB089 and WB090 using a plasmid pKD3 (No. 7631, purchased from CGSC, U.S.) as the template, and 1166 bp was recovered by cutting the gel to obtain a PCR product of the chloramphenicol resistance gene.

The strain TOP10/pKD46 was cultured in an LB medium at 30° C.; induction was performed for 1 hour by adding arabinose at a final concentration of 100 mM when $OD_{600}$ was 0.2; 40 µL of competent cells were transformed using 5 µL of the recovered PCR product of the chloramphenicol resistance gene after the competent cells were prepared, and a recovered product was coated on an LB plate containing 34 µg/mL of chloramphenicol after 1 h recovery at 30° C. and was cultured at 37° C. overnight. Recombinants were picked and subject to colony PCR identification using primers WB064 and WB065. The PCR product of a positive recombinant should have a size of 1816 bp, while the original gene had a size of 1980 bp. Positive recombinants were picked and were subject to continuous culture in an LB liquid culture medium at 42° C. for three passages to eliminate plasmid pKD46 and obtain a strain TOP10 dcm::CmR.

A single colony of the strain TOP10 dcm::CmR was picked after dilution and plate coating to prepare an electrotransformation competent strain; a plasmid pCP20 (No.

Figure 1:
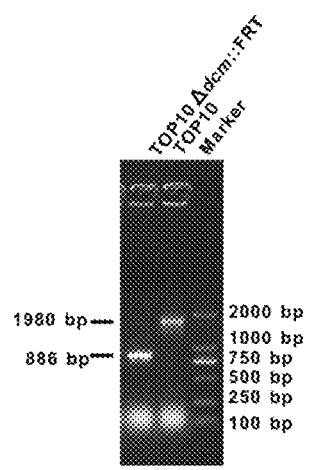
FIG. 1 shows a PCR detection result of gene dcm knockout of TOP10.

7629, purchased from CGSC, U.S.) was transformed into the strain TOP10 dcm::CmR; after screening for recombinants with ampicillin-resistant recombinants, a single colony was cultured in an LB medium without antibiotics at 30° C. until $OD_{600}$ 0.2, and then temperature was increased to 42° C. for overnight culture. A non-resistant LB plate was coated after bacterial solution was diluted, and a single colony was picked and subject to colony PCR identification using primers WB064 and WB065. The amplification product of a positive recombinant with chloramphenicol resistance gene eliminated should have a size of 886 bp (FIG. 1), and this positive recombinant was designated as TOP10Δdcm::FRT.

Since a double-mutation of dam and recA is a lethal genotype, reversion of gene recA1 was first performed before gene dam was knocked out. Wild-type gene recA (1236 bp) was amplified with primers WB253 and WB254 using chromosomal DNA of *E. coli* W3110 (No. 4474, purchased from CGSC, U.S.) as the template, and was ligated to sites NotI and BamHI of vector pKOV (Catalog No. 25769, purchased from Addgene, U.S.) to obtain pKOV-recA. pKOV-recA was transformed into the strain TOP10Δdcm::FRT, chloramphenicol-resistant transformants were screened at 30° C., transformants were picked and subsequently cultured overnight in a liquid LB medium at 42° C., and an LB plate containing chloramphenicol was coated to allow pKOV-recA to be integrated into the site recA1 of the chromosome. After a single colony is obtained, colony PCR was performed using primers WB255 and WB256. If there is a PCR band greater than 7 Kb, it is demonstrated that pKOV-recA has been integrated into the chromosome. Correct recombinants were picked and coated on an LB plate containing 10% sucrose after culturing at 42° C., a single colony was lined on both an LB plate with chloramphenicol and an LB plate without chloramphenicol for simultaneous passage, and chloramphenicol-sensitive colonies were picked. Gene recA was amplified using primers WB255 and WB256 and sequencing was performed, and the base at site 482 of gene recA of recA+recombinant should be G, while that of the strain TOP10 is A.

Figure 2:
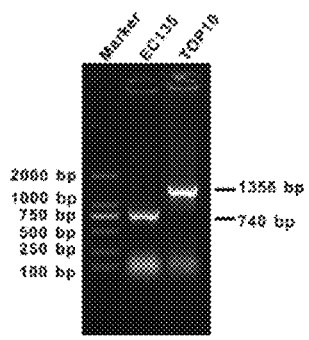
FIG. 2 shows a PCR detection result of gene dam knockout of EC135.

The steps of knockout of gene dam were the same as those of dcm, and amplification primers for the chloramphenicol resistance gene were WB087 and WB088, and outer detection primers were WB062 and WB063. The amplification product had a size of 740 bp after genes were knocked out, while the original gene had a size of 1356 bp (FIG. 2).

Through the three steps of genetic manipulations described above, the resultant strain with dcm and dam deleted and recA reverse-mutated was EC135.

The above-mentioned strain EC135 was deposited in China General Microbiological Culture Collection Center (simply referred to as CGMCC; Address: No. 1 Beichen West Road, Chaoyang District, Beijing, Institute Of Microbiology Chinese Academy of Sciences, Postal Code 100101) on Mar. 21, 2012, with a Deposit No. of CGMCC No. 5925, and the category thereof was designated as *Escherichia coli*.

See Table 1 for the sequences of the primers used.

TABLE 1

PCR primers used in the invention

| Name of Primer | Sequence of Primer (5'-3') |
| --- | --- |
| WB089 | CTAAATGGCTGTAATTATGTTAACCTGTCGGCCATCTCAGATGGCCGGT GAAATCTTTGAGCGATTGTGTAGGCTGGAG |
| WB090 | ACCGGAATACGGAATTTCGCTTCTCCCGGCGCTTCAAAACCCATTAAGC GCGCGCATAACGGCTGACATGGGAATTAGC |
| WB064 | TGCTGAAGCTACCGCAAACCATG |
| WB065 | GCACTCCCAGACAATCAATACGC |
| WB253 | ATAAGAATGCGGCCGCCACTTGATACTGTATGAGCATACAG |
| WB254 | CGCGGATCCCGGGATGTTGATTCTGTCATGGCAT |
| WB255 | ATTACCCGGCGGGAATGCTTCAG |
| WB256 | TTTACGTCGCAGTTCTTGCTCAC |
| WB087 | CTGGATGCTGTCGGAGCTTTCTCCACAGCCGGAGAAGGTGTAATTAGTTA GTCAGCTTGAGCGATTGTGTAGGCTGGAG |
| WB088 | ACTTTGACGACATGCAATTTTGCGCGCTGATACCACTCACGCGTTAACAT CGTATCTAACGGCTGACATGGGAATTAGC |
| WB062 | GGCCGATCTGAAGTAATCAAGGT |
| WB063 | TCCAGATAGCTCAGAGGTGTCGC |
| WB325 | ATGCCATAGCATTTTTATCC |
| WB475 | CGTAGTTTATTCATGAATTCCTCCTTCAACTATGTACTTGAGGTAATCGA |
| WB476 | TCGATTACCTCAAGTACATAGTTGAAGGAGGAATTCATGAATAAACTACG |
| WB477 | TTATTGCTGTTCATGAATTCCTCCTTTATTCAGATTCTTTATTATCGTAT |
| WB478 | ATACGATAATAAAGAATCTGAATAAAGGAGGAATTCATGAACAGCAATAA |
| WB479 | GAAAAAAACGCATGAATTCCTCCTTATTCTAAATCTAATAATTCATTT |

TABLE 1 -continued

PCR primers used in the invention

| Name of Primer | Sequence of Primer (5'-3') |
|---|---|
| WB480 | AAATGAATTATTAGATTTAGAATAAAGGAGGAATTCATGCGTTTTTTTTC |
| WB326 | GATTTAATCTGTATCAGG |
| WB325 | |
| WB575 | ATACAGTTCATATGTCTTACCTCCTTTAATCGGCGGTATTTTGTGTAGAT |
| WB576 | ATCTACACAAAATACCGCCGATTAAAGGAGGTAAGACATATGAACTGTAT |
| WB577 | TTTAAACATATAACACTTTCCTCCTTTACGCTTCTAATGTCTCTCGAATG |
| WB578 | CATTCGAGAGACATTAGAAGCGTAAAGGAGGAAAGTGTTATATGTTTAAA |
| WB579 | AATCTATCATTTAAAAACACCTCTMTCTACTCAACTAACATTAAGTAGA |
| WB580 | TCTACTTAATGTTAGTTGAGTAGACAAGAGGTGTTTTTAAATGATAGATT |
| WB581 | ATATCATAATATCACTCTCCCTCCTCTCAATAGCTAATTCTTCTTTAAAC |
| WB582 | GTTTAAAGAAGAATTAGCTATTGAGAGGAGGGAGAGTGATATTATGATAT |
| WB583 | CTATCAACATACTTTTCCACCGCCTTCATTCTTTAATACTTGGCTCTACG |
| WB584 | CGTAGAGCCAAGTATTAAAGAATGAAGGCGGTGGAAAAGTATGTTGATAG |
| WB326 | |
| WB325 | |
| WB585 | TCGATTCCGTGCATGAATTCCTCCTTTATGCCGCAAGTCTCCGGGCGGCG |
| WB586 | CGCCGCCCGGAGACTTGCGGCATAAAGGAGGAATTCATGCACGGAATCGA |
| WB587 | GGATGTTATGCATACGACACCTCCTTCAGAGACTACGCACGTCGAGAATG |
| WB588 | CATTCTCGACGTGCGTAGTCTCTGAAGGAGGTGTCGTATGCATAACATCC |
| WB589 | CGCGACACACCCATGAATTCCTCCTTCATTTGCCACCTCCATCGGTAGAT |
| WB590 | ATCTACCGATGGAGGTGGCAAATGAAGGAGGAATTCATGGGTGTGTCGCG |
| WB326 | |
| WB607 | CAAGGCGGACCGCTTATGCATG |
| WB608 | CTTTAGTTGAAGCAAATACGTAAACCTTTCCCAT |
| WB609 | TTTACGTATTTGCTTCAACTAAAGCACCCATTAGTTC |
| WB610 | AGTCTGTCACCCAACCTTCTTCAACTAACGGGGCAGG |
| WB611 | TTGAAGAAGGTTGGGTGACAGACTGTACGGAAC |
| WB612 | TCCCGAGTGATCGTATGGAC |
| WB605 | AACACTTCGCGGACCGCGCG |
| WB606 | TGCCACACTGACTTTGTCGG |
| WB654 | TACGCGTCGACCGCTGATCACACGATAGTCGGCG |
| WB655 | TCCTTTACTCATGATCCCTCGTCCTCAGATCCAT |
| WB656 | GGACGAGGGATCATGAGTAAAGGAGAAGAACTT |
| WB650 | TGCAACTGCAGTTATTTGTATAGTTCATCCAT |

Examples 2

The Introduction of an Exogenous DNA Molecule into *Bacillus amyloliquefaciens* TA208 by Overcoming the Restriction Modification Barrier I. The Construction of Recombinant Bacterium Co-Expressing all DNA-methyltransferase-encoding genes of TA208

1. The Achievement of DNA-methyltransferase-Encoding Genes of Strain TA208

1) the Prediction of DNA-methyltransferase-Encoding Genes of Strain TA208

Figure 3:
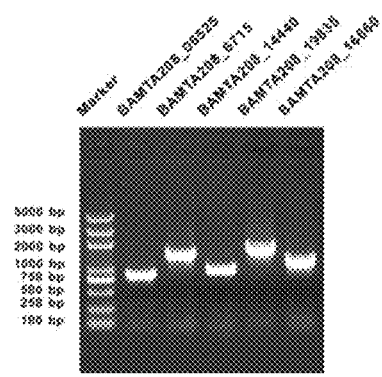
FIG. 3 shows PCR amplification results of DNA methyltransferase genes of *Bacillus amyloliquefaciens* TA208.

Genome-wide sequences of the strain TA208 have been determined and its GenBank No. is CP002627. There are in total 5 putative DNA-methyltransferase-encoding genes on its chromosome, locus tags of these genes are BAMTA208_06525, BAMTA208_6715, BAMTA208_14440, BAMTA208_19835, and BAMTA208_16660, respectively. PCR amplification results of five gene fragments were shown in FIG. 3.

2) the Verification of DNA-methyltransferase-Encoding Genes of Strain TA208

The five genes described above were respectively cloned to sites between NcoI and XbaI, EcoRI and XbaI, EcoRI and XbaI, EcoRI and SalI, and EcoRI and SalI of plasmid pBAD43 (Tight regulation, modulation, and high-level expression by vectors containing the arabinose PBAD promoter. L M Guzman, D Belin, M J Carson, J. Beckwith. Journal of Bacteriology, 1995 177:4121-30, publically available from Institute Of Microbiology Chinese Academy of Sciences), so as to obtain a plasmid pBAD43 containing BAMTA208_06525, a plasmid pBAD43 containing BAMTA208 6715, a plasmid pBAD43 containing BAMTA208_14440, a plasmid pBAD43 containing BAMTA208_19835, and a plasmid pBAD43 containing BAMTA208_16660; and the 5 types of plasmids were respectively transformed into *E. coli* EC135 to obtain recombinant bacteria 1-5. Plasmids of recombinant bacteria 1-5 were extracted and sent for sequencing in order to verify correctness, and consequently the recombinant bacteria were positive recombinant bacteria.

Dot hybridization verification: the recombinant bacteria 1-5 verified to be positive were induced to express methyltransferases (arabinose at a final concentration of 0.2% by mass was added after culturing in an LB medium until $OD_{600}$ 0.2, and induction was performed at 30° C. for 12 hours), and then total DNAs were extracted using DNeasy Blood and Tissue Kit (Qiagen) to obtain DNA1-DNA5. DNA1-DNA5 obtained above were respectively boiled for 3 min to be denaturized into single strands, which were subsequently inserted into an ice-water mixture for quenching. EC135/pBAD43 (pBAD43 transferred into EC135) was used as a negative control.

Total DNAs of EC135/pBAD43 and 5 samples DNA1-DNA5 were all spotted onto a Protran BA85 nitrocellulose film (Whatman) at 450 ng, 150 ng, and 50 ng, which was repeated on three films. The films were placed in 5% skim milk powder formulated with TBST (200 mM NaCl, 0.1% Tween20, 50 mM Tris-HCl, pH7.4) after 2 min UV crosslinking, and were blocked at room temperature (25° C.) for 1 hour. Three films were then placed into a hybridization bag, and 10 mL 1:10000 diluted rabbit anti-N6 mA serum (New England Biolabs), 10 mL 1:10000 diluted rabbit anti-N4mC serum (New England Biolabs), and 10 mL 1:20000 diluted mouse anti-5mC monoclonal antibody (Zymo Research, Catalog No.A3001-50) were added, respectively. The films were washed 5 times with TBST after incubation for 1 hour at room temperature (25° C.), and corresponding horse radish peroxidase labeled goat anti-rabbit second antibody (Catalog No. 111-035-003, Jackson ImmunolResearch, U.S.) or goat anti-mouse second antibody (Catalog No. 81-6520, Zymed, U.S.), with a dilution of 1:10000, was added after the films were placed into the hybridization bag. The films were washed 5 times with TBST after incubation for 1 hour at room temperature. Solutions A and B (each 0.5 mL) of an ECL reagent (Catalog No. RPN2232, Amersham) were uniformly mixed and evenly dropped on the surfaces of the films. Fluorescence signal was exposed to X-ray films in a dark room.

Figure 4:
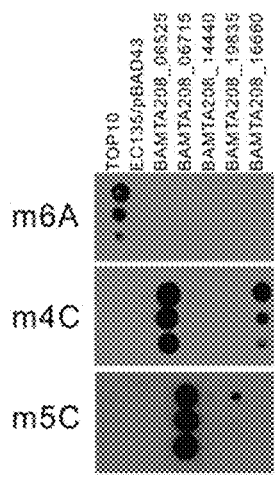
FIG. 4 shows a dot hybridization which detects the activities of DNA methyltransferase of *Bacillus amyloliquefaciens* TA208.

Results were shown in FIG. 4 (in which m6A/m4C/m5C were results of hybridizations using different antibodies). It can be seen that BAMTA208_06525, BAMTA208_6715, BAMTA208_19835, and BAMTA208_16660 have activities of methylation modification and are DNA methyltransferase genes.

2. The Achievement of Recombinant Bacterium Co-Expressing all DNA-methyltransferase-encoding Genes 1) Construction Using a plasmid pBAD43 containing BAMTA208_06525 (SEQ ID NO: 2), a plasmid pBAD43 containing BAMTA208_6715 (SEQ ID NO: 3), a plasmid pBAD43 containing BAMTA208_19835 (SEQ ID NO: 4), and a plasmid pBAD43 containing BAMTA208_16660 (SEQ ID NO: 5) as templates respectively, with WB325 and WB475 (having a size of 839 bp, FIG. 3) as primers used for BAMTA208_06525, WB476 and WB477 (having a size of 1512 bp, FIG. 3) as primers used for BAMTA208_6715, WB478 and WB479 (having a size of 1794 bp, FIG. 3) as primers used for BAMTA208_19835, and WB480 and WB326 (having a size of 1272 bp, FIG. 3) as primers used for BAMTA208_16660, the sequences of the primers being shown in Table 1, PCR amplification was performed to obtain 4 PCR products respectively.

The 4 PCR products were respectively recovered by cutting the gel, and equal amounts of the 4 PCR products were mixed and concentrated to a total volume 50 μL to obtain PCR total products.

Figure 5:
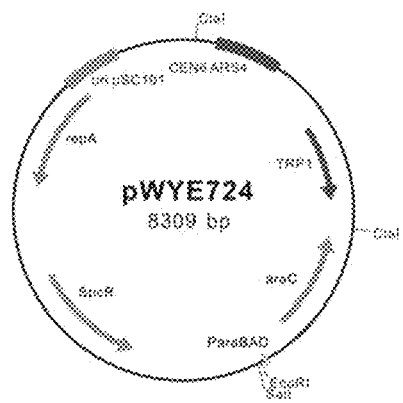
FIG. 5 shows a plasmid map of pWYE724.
Figure 6:
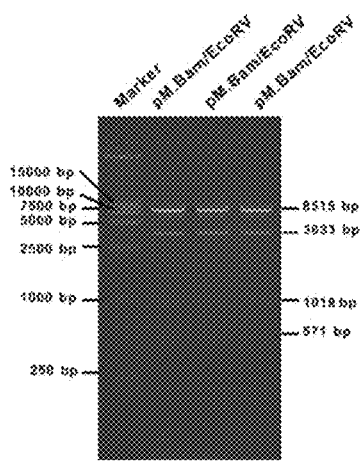
FIG. 6 shows an electrophoretogram of pM.Bam detected by EcoRV single cleavage.
Figure 7:
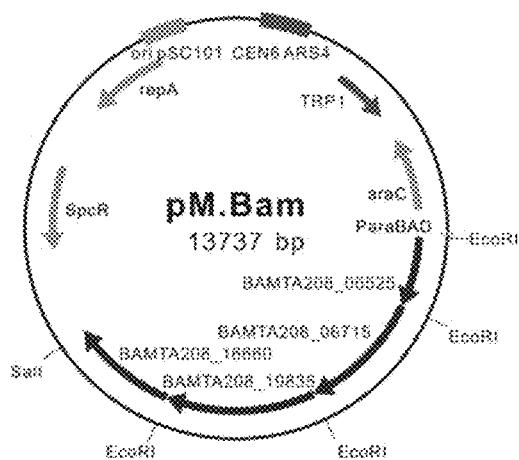
FIG. 7 shows a plasmid map of pM.Bam.

500 ng of plasmid pWYE724 (see FIG. 5 for the plasmid map, and the sequence thereof is SEQ ID NO: 1) was double-cleaved by EcoRI and SalI, and was mixed with the PCR total products described above after being recovered by cutting, and then by using a lithium acetate transformation method (Methods in Enzymology, 350, 87-96.), *Saccharomyces cerevisiae* DAY414 was transformed (Mds3 regulates morphogenesis in *Candida albicans* through the TOR pathway, Zacchi L F, Gomez-Raja J, Davis D A, Molecular and Cellular Biology, 2010, 30: 3695-3710, publically available from Institute Of Microbiology Chinese Academy of Sciences). Transformants were screened on a plate of a complete synthetic culture medium without tryptophan added (SC trp-, Beijing FunGenome Co., Ltd.). A single colony was picked into a YPD culture medium, and a yeast plasmid was extracted using a glass bead method (Nucleic Acids Research, 20, 3790). The plasmid was transformed into *E. coli* TOP10, transformants were screened using an LB plate containing 100 μg/mL spectinomycin, and EcoRV single cleavage was performed after the plasmid was extracted. A correct recombinant plasmid should generate four bands 8515 bp, 3633 bp, 1018 bp, and 571 bp (as shown in FIG. 6), which was designated as pM.Bam (the structural schematic diagram was shown in FIG. 7), and was sent for sequencing to demonstrate that the results were correct.

The plasmid pM.Bam was transformed into the strain EC135 obtained in example 1, and cleavage verification was performed according to the method described above. The correct transformant was EC135/pM.Bam, which was a host precisely simulated in a pattern of *Bacillus amyloliquefaciens* TA208 DNA methylation.

2) Verification

In order to detecting the effectiveness of methylation simulation, methyltransferase genes in EC135/pM.Bam were allowed to be expressed by inducing at 30° C. for 12 hours using arabinose at a final concentration of 0.2%. Total DNAs were extracted and dot hybridization detection was performed using chromosomal DNA of the strain TA208 as a control according to the method described above in 1, and the result was that there was no significant difference in the hybridization between EC135/pM.Bam and TA208, which demonstrated that methyltransferases were all expressed, and which demonstrated that EC135/pM.Bam is a recombinant bacterium co-expressing all DNA-methyltransferase-encoding genes.

II. The Introduction of an Exogenous DNA Molecule into a Target Bacterium by Overcoming Restriction Modification Barrier 1. The Introduction of Shuttle Plasmid into a Target Bacterium by Overcoming Restriction Modification Barrier A. Introduction 1) Shuttle plasmid pAD43-25 (7262 bp, Catalog No. ECE166, purchased from *Bacillus* Genetic Stock Center, U.S., simply referred to as BGSC below) was transformed into EC135/pM.Bam obtained in "I" to obtain recombinant bacteria respectively.

2) The recombinant bacteria were subject to arabinose induction (in which induction was performed at 30° C. for 12 hours using arabinose at a final concentration of 0.2%) to obtain induced recombinant bacteria.

3) Plasmids of the induced recombinant bacteria were extracted (wherein the plasmids include pM.Bam and shuttle plasmids, while pWYE724 is a low-copy plasmid, pM.Bam has a copy number of about 5/cell, and the shuttle plasmid has a copy number of about 300/cell), and *Bacillus amyloliquefaciens* TA208 was transformed (Complete genome sequence of *Bacillus amyloliquefaciens* TA208, a strain for industrial production of guanosine and ribavirin, Guoqiang Zhang, Aihua Deng, Qingyang Xu, Yong Liang, Ning Chen, Tingyi Wen, Journal of Bacteriology, 193 (12):3142-3143) using a method as recorded in Analytical Biochemistry, 409, 130-137, to obtain TA208/pAD43-25 (EC135/pM.Bam).

Using the same method, shuttle plasmid pAD43-25 was respectively transferred into TOP10 and EC135, and was then transferred into TA208 after modification to obtain TA208/pAD43-25 (TOP10) and TA208/pAD43-25 (EC135) respectively.

Using the same method, shuttle plasmids pAD123 (5952 bp, No. ECE165, purchased from BGSC, U.S.), pMK3 (7214 bp, No. ECE15, purchased from BGSC, U.S.), pMK4 (5585 bp, No. ECE16, purchased from BGSC, U.S.), pHCMC02 (6866 bp, No. ECE188, purchased from BGSC, U.S.), pHCMC04 (8089 bp, No. ECE189, purchased from BGSC, U.S.), and pDG148StuI (8272 bp No. ECE145, purchased from BGSC, U.S.) were respectively transferred into EC135/pM.Bam, TOP10, and EC135, and were then transferred into TA208 after modification to obtain the following, respectively:

TA208/pAD123 (EC135/pM.Bam), TA208/pAD123 (TOP10), and TA208/pAD123 (EC135),

TA208/pMK3 (EC135/pM.Bam), TA208/pMK3 (TOP10), and TA208/pMK3 (EC135),

TA208/pMK4 (EC135/pM.Bam), TA208/pMK4 (TOP10), and TA208/pMK4 (EC135), TA208/pHCMC02 (EC135/pM.Bam), TA208/pHCMC02 (TOP10), and TA208/pHCMC02 (EC135), TA208/pHCMC 04 (EC135/pM.Bam), TA208/pHCMC 04 (TOP10), and TA208/pHCMC 04 (EC135), TA208/pDG148StuI (EC135/pM.Bam), TA208/pDG148StuI (TOP10), and TA208/pDG148StuI (EC135).

B. The Calculation of Transformation Efficiency

TA208/pAD43-25 (EC135/pM.Bam), TA208/pAD43-25 (TOP10), TA208/pAD43-25 (EC135), TA208/pAD123 (EC135/pM.Bam), TA208/pAD123 (TOP10), TA208/pAD123 (EC135), TA208/pMK3 (EC135/pM.Bam), TA208/pMK3 (TOP10), TA208/pMK3 (EC135), TA208/pMK4 (EC135/pM.Bam), TA208/pMK4 (TOP10), TA208/pMK4 (EC135), TA208/pHCMC02 (EC135/pM.Bam), TA208/pHCMC02 (TOP10), TA208/pHCMC02 (EC135), TA208/pHCMC 04 (EC135/pM.Bam), TA208/pHCMC 04 (TOP10), TA208/pHCMC 04 (EC135), TA208/pDG148StuI (EC135/pM.Bam), TA208/pDG148StuI (TOP10), and TA208/pDG148StuI (EC135). Using the number of single colonies on the coated plate after transformation with the above, according to the amount of DNA of shuttle plasmids used (since the copy number of pM.Bam was too low, the total amount of plasmids added was the amount of DNA of shuttle plasmids), the transformation efficiency was calculated. 4 transformants were picked randomly for DNA verification by extracting plasmids. The experiment was repeated three times and the results showed the average value±the standard deviation.

The transformation efficiency is: the number of single colonies (CFU)×(the volume of recovered solution after transformation/the volume of coated bacterial solution)×the dilution ratio of recovered solution/the amount of shuttle plasmids used in transformation (µg).

Figure 8:
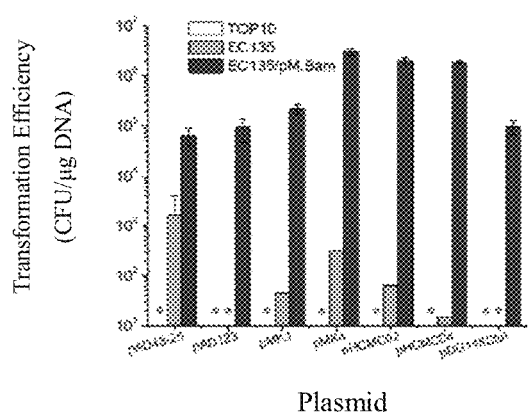
FIG. 8 shows the transformation efficiency of *Bacillus amyloliquefaciens* TA208 by shuttle plasmids prepared from different hosts (* undetected).

Results were shown in FIG. 8, and it can be seen:

the transformation efficiency for TA208/pAD43-25 (EC135/pM.Bam) is $6.4\pm2.6\times10^5$CFU/µg DNA;

the transformation efficiency for TA208/pAD43-25 (TOP10) was 0;

the transformation efficiency for TA208/pAD43-25 (EC135) was $2.4\pm1.6\times10^3$CFU/µg DNA;

the transformation efficiency for TA208/pAD123 (EC135/pM.Bam) was $9.1\pm4.3\times10^5$CFU/µg DNA;

the transformation efficiency for TA208/pAD123 (TOP10) was 0;

the transformation efficiency for TA208/pAD123 (EC135) was 0;

the transformation efficiency for TA208/pMK3 (EC135/pM.Bam) was $2.2\pm0.5\times10^5$CFU/µg DNA;

the transformation efficiency for TA208/pMK3 (TOP10) was 0;

the transformation efficiency for TA208/pMK3 (EC135) was $4.5\times10^1$CFU/µg DNA;

the transformation efficiency for TA208/pMK4 (EC135/pM.Bam) was $3.0\pm0.4\times10^6$CFU/µg DNA;

the transformation efficiency for TA208/pMK4 (TOP10) was 0;

the transformation efficiency for TA208/pMK4 (EC135) was $3.1\times10^2$CFU/µg DNA;

the transformation efficiency for TA208/pHCMC02 (EC135/pM.Bam) was $2.0\pm0.3\times10^6$CFU/µg DNA;

the transformation efficiency for TA208/pHCMC02 (TOP10) was 0;

the transformation efficiency for TA208/pHCMC02 (EC135) was $6.3\times10^1$CFU/µg DNA;

the transformation efficiency for TA208/pHCMC 04 (EC135/pM.Bam) was 1.9±0.1×10$^6$CFU/μg DNA;

the transformation efficiency for TA208/pHCMC 04 (TOP10) was 0;

the transformation efficiency for TA208/pHCMC 04 (EC135) was 1.5×10$^1$CFU/μg DNA;

the transformation efficiency for TA208/pDG148StuI (EC135/pM.Bam) was 9.7±3.2×10$^4$CFU/μg DNA;

the transformation efficiency for TA208/pDG148StuI (TOP10) was 0; and the transformation efficiency for TA208/pDG148StuI (EC135) was 0.

Plasmids prepared by TOP10 cannot transform the strain TA208, plasmids prepared in the strain EC135 had a transformation efficiency at a level of 0-10$^3$CFU/μg DNA, and shuttle plasmids prepared in EC135/pM.Bam had a transformation efficiency at a level of 10$^4$-10$^6$CFU/μg DNA.

Plasmids of single colonies for each strain were extracted simultaneously and an electrophoretic or sequencing comparison with a plasmid before transformation was performed, and the result showed an identical size and demonstrated that these strains were positive plasmids in which an exogenous DNA molecule was transferred.

2. The Introduction of Integration Plasmid into a Target Bacterium

The method for preparing an integration plasmid pWYE748 containing a homologous arm of gene upp and chloramphenicol resistance gene was as follows: Using primers WB607 and WB608 as the primers and chromosomal DNA of TA208 as the template, a homologous arm 641 bp upstream of gene upp was subject to PCR amplification; using WB609 and WB610 as primers and a plasmid pMK4 as the template, chloramphenicol resistance gene 906 bp was subject to amplification; using WB611 and WB612 as the primers and chromosomal DNA of TA208 as the template, a homologous arm 669 bp downstream of gene upp was subject to PCR amplification; and the three stages of the PCR products were recovered by cutting the gel, and were then mixed (1 μL each) and used as templates. PCR was performed again using WB607 and WB612 as primers to obtain a fragment of 2216 bp. The PCR product was cloned to a plasmid pMD19-T (Catalog No. D106A, Taraka), and the resultant plasmid was the integration plasmid pWYE748.

Using the transformation method described above in 1, the integration plasmid pWYE748 was modified in EC135/pM.Bam, and then the strain TA208 was transformed and chloramphenicol-resistant transformants were screened.

Figure 9:
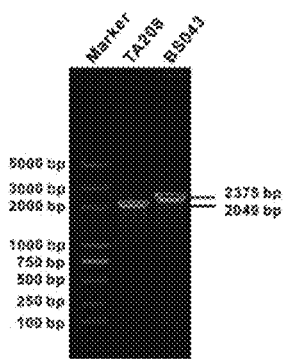
FIG. 9 shows a PCR verification result for gene upp knockout of *Bacillus amyloliquefaciens* TA208.

Amplification identification was performed with primers WB605 and WB606, using DNA of the transformant and genomic DNA of wild-type TA208 as the templates. The results of amplification were shown as in FIG. 9, and the amplification size of the transformant was 2375 bp (gene upp was inserted into the chloramphenicol resistance gene), while the original size of chloramphenicol resistance gene of wild-type TA208 was 2049 bp, which demonstrated that an exogenous gene was transferred and the integration was successful, and the transformant was designated as BS043.

Gene upp encodes uracil phosphoribosyl transferase, by which 5-fluorouracil is converted into 5-fluorouracil nucleoside monophosphate and eventually metabolized into a toxic metabolite 5-fluorouracil nucleoside diphosphate, which strongly inhibits the activity of thymidylate synthase and results in death of bacteria.

Figure 10:
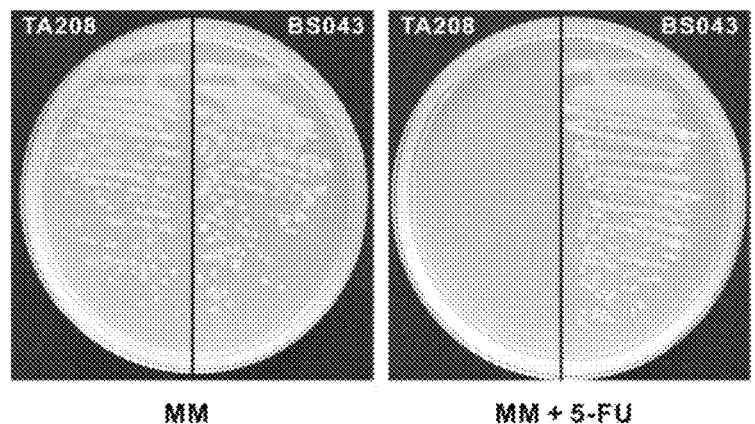
FIG. 10 shows growth situations of *Bacillus amyloliquefaciens* TA208 and BS043 in culture media MM and MM+5-FU.

It is further demonstrated whether BS043 has included an exogenous gene, and the method thereof is: Strains BS043 were grown on MM culture media (see Molecular Microbiology, 46, 25-36. for the components of the culture media, and 100 mg/L adenosine was added) with/without 10 μM 5-fluorouracil (Catalog No. F6627, Sigma) added, and a strain TA208 was used as a control. Results were shown in FIG. 10, and it can be seen: BS043 can grow on the culture medium with 10 μM 5-fluorouracil added, which demonstrated that an exogenous gene was transferred and the integration was successful.

However, in EC135 and TOP10, TA208 was transformed several times by the extracted integration plasmid pWYE748 and it failed to obtain any transformant.

Example 3

The Introduction of an Exogenous DNA Molecule into *Bacillus cereus* ATCC 10987 by Overcoming Restriction Modification Barrier I. The Construction of Recombinant Bacterium Co-Expressing all DNA-methyltransferase-Encoding Genes of ATCC 10987

1. The Achievement of DNA-methyltransferase-Encoding Genes of Strain ATCC 10987

1) the Prediction of DNA-methyltransferase-Encoding Genes of Strain ATCC 10987

Genome-wide sequences of the strain ATCC 10987 have been disclosed and its GenBank No. is AE017194. There are total 9 putative DNA-methyltransferase-encoding genes on its chromosome, locus tags of these genes are BCE_0841-BCE_0842, BCE_0839-BCE_0842, BCE_0365, BCE_0392, BCE_0393, BCE_4605, BCE_5606, BCE_5607, and BCE_1018, respectively.

2) the Verification DNA-methyltransferase-Encoding Genes of Strain ATCC 10987 BCE_0841-BCE_0842, BCE_0839-BCE_0842, BCE_0365, BCE_0392, BCE_0393, BCE_4605, BCE_5606, BCE_5607, and BCE_1018 were respectively cloned to sites between NheI and KpnI, NcoI and KpnI, NheI and KpnI, NheI and KpnI, NheI and KpnI, NheI and KpnI, NheI and KpnI, NheI and XbaI, and NheI and KpnI of a plasmid pBAD43, so as to obtain a plasmid pBAD43 containing BCE_0841-BCE_0842, a plasmid pBAD43 containing BCE_0839-BCE_0842, a plasmid pBAD43 containing BCE_0365, a plasmid pBAD43 containing BCE_0392, a plasmid pBAD43 containing BCE_0393, a plasmid pBAD43 containing BCE_4605, a plasmid pBAD43 containing BCE_5606, a plasmid pBAD43 containing BCE_5607, and a plasmid pBAD43 containing BCE_1018.

The aforementioned types of plasmids were respectively transformed into *E. coli* EC135 to obtain recombinant bacteria 1-9.

Plasmids of recombinant bacteria 1-9 were extracted and sent for sequencing in order to verify correctness, and consequently the recombinant bacteria are positive recombinant bacteria.

Dot Hybridization Verification:

After the recombinant bacteria 1-9 verified to be positive were induced to express methyltransferases (arabinose at a final concentration of 0.2% was used and induction was performed at 30° C. for 12 hours), total DNAs were extracted using DNeasy Blood and Tissue Kit (Qiagen) to obtain DNA1-DNA9. DNA1-DNA9 obtained above were boiled for 3 min to be denaturized into single strands, which were subsequently inserted into an ice-water mixture for quenching. EC135/pBAD43 was used as a negative control.

Total DNAs of EC135/pBAD43 and 9 samples DNA1-DNA9 were all spotted onto a Protran BA85 nitrocellulose film (Whatman) at 450 ng, 150 ng, and 50 ng, which was repeated on three films. The films were placed in 5% skim milk powder formulated with TBST (200 mM NaCl, 0.1% Tween20, 50 mM Tris-HCl, pH7.4) after 2 min UV cross-linking, and were blocked at room temperature for 1 hour. Three films were then placed into a hybridization bag and 10 mL 1:10000 diluted rabbit anti-N6 mA serum, 10 mL 1:10000 diluted rabbit anti-N4mC serum, and 10 mL 1:20000 diluted mouse anti-5mC monoclonal antibody, were added, respectively. The films were washed 5 times after incubation for 1 hour at room temperature, and corresponding goat anti-rabbit second antibody or goat anti-mouse second antibody, with a dilution ratio of 1:10000, was added after the films were placed into the hybridization bag. The films were washed 5 times after incubation for 1 hour at room temperature. Solutions A and B (each 0.5 mL) of an ECL reagent were uniformly mixed and evenly dropped on the surfaces of the films. Fluorescence signal was exposed to X-ray films in a dark room.

Figure 11:
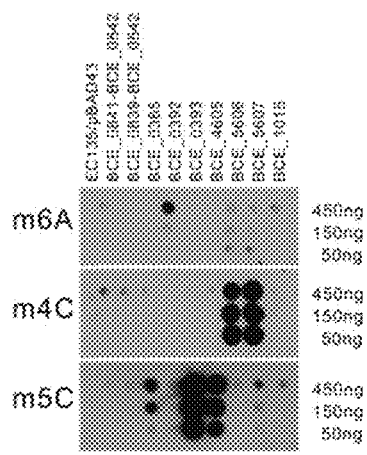
FIG. 11 shows a dot hybridization which detects the activities of DNA methyltransferases of *Bacillus cereus* ATCC 10987.

Results were shown in FIG. 11 (in which m6/m4C/m5C were results of hybridizations using different antibodies). It can be seen that BCE_0393, BCE_4605, BCE_5606, BCE_5607, BCE_0365, and BCE_0392 have activities of methylation modification and are DNA methyltransferase genes.

2. The Achievement of Recombinant Bacterium Co-Expressing all DNA-Methyltransferase-Encoding Genes 1) Construction Using a plasmid pBAD43 containing BCE_0393 (SEQ ID NO: 6), a plasmid pBAD43 containing BCE_4605 (SEQ ID NO: 7), a plasmid pBAD43 containing BCE_5606 (SEQ ID NO: 8), a plasmid pBAD43 containing BCE_5607 (SEQ ID NO: 9), a plasmid pBAD43 containing BCE_0365 (SEQ ID NO: 10), and a plasmid pBAD43 containing BCE_0392 (SEQ ID NO: 11) as templates respectively, with WB325 and WB575 (having a size of 2160 bp) as primers used for BCE_0393, WB576 and WB577 (having a size of 1102 bp) for BCE_4605, WB578 and WB579 (having a size of 1345 bp) for BCE_5606, WB580 and WB581 (having a size of 1316 bp) for BCE_5607, WB582 and WB583 (having a size of 1071 bp) for BCE_0365, and WB584 and WB326 (having a size of 1257 bp) for BCE_0392, the sequences of the primers being as shown in Table 1, PCR amplification was performed to obtain 6 PCR products respectively.

The 6 PCR products were respectively recovered by cutting the gel, and equal proportions of the 6 PCR products were mixed and concentrated to a total volume 50 μL to obtain PCR total products.

Figure 12:
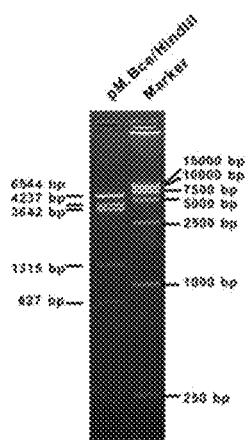
FIG. 12 shows an electrophoretogram of pM.Bce detected by HindIII single cleavage.
Figure 13:
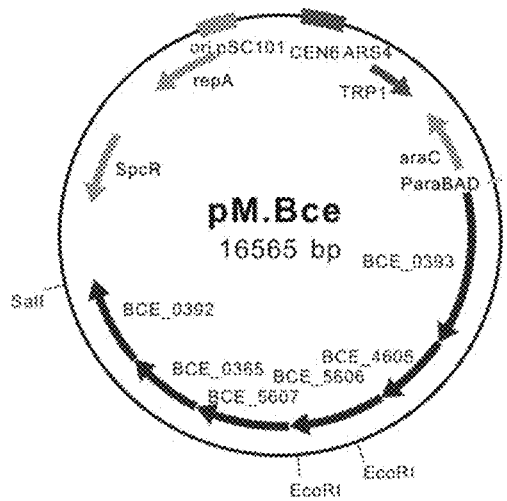
FIG. 13 shows a plasmid map of pM.Bce.

500 ng of plasmid pWYE724 was double-cleaved by EcoRI and SalI, and was mixed with the PCR total products described above after being recovered by cutting, and then by using a lithium acetate transformation method (Methods in Enzymology, 350, 87-96.), Saccharomyces cerevisiae DAY414 was transformed. Transformants were screened on a plate of a complete synthetic culture medium without tryptophan added (SC trp-, Beijing FunGenome Co., Ltd.). A single colony was picked into a YPD culture medium, and a yeast plasmid was extracted using a glass bead method (Nucleic Acids Research, 20, 3790). The plasmid was transformed into E. coli TOP10, transformants were screened using an LB plate containing 100 μg/mL spectinomycin, and HindIII single cleavage was performed after the plasmid was extracted. A correct recombinant plasmid should generate five bands 6544 bp, 4237 bp, 3642 bp, 1315 bp, and 827 bp (as shown in FIG. 12), which was designated as pM.Bce (the structural schematic diagram was shown in FIG. 13), and was sent for sequencing to demonstrate that the result was correct.

The plasmid pM.Bce was transformed into the strain EC135 obtained in example 1, and cleavage verification was performed according to the method described above. The correct transformant is EC135/pM.Bce, which is a host precisely simulated in a pattern of Bacillus cereus ATCC 10987 DNA methylation.

2) Verification

In order to detecting the effectiveness of methylation simulation, methyltransferase genes were allowed to be expressed by inducing EC135/pM.Bce at 30° C. for 12 hours using arabinose induction with a final concentration of 0.2%. Total DNAs were extracted and dot hybridization detection was performed using chromosomal DNA of the strain ATCC 10987 as a control according to the aforementioned method, and the result was that there was no significant difference in the hybridization between EC135/pM.Bce and ATCC 10987, which demonstrated that methyltransferases were all expressed, and which demonstrated that EC135/pM.Bce was a recombinant bacterium co-expressing all DNA-methyltransferase-encoding genes.

II. The Introduction of Shuttle Plasmid into a Target Bacterium by Overcoming Restriction Modification Barrier Shuttle plasmids were respectively transferred into EC135/pM.Bce, EC135, and TOP10, the plasmids were extracted after arabinose induction (see aforementioned methods), and strains ATCC 10987 were respectively transformed using the same method as in "I" of Example 2. The shuttle plasmids described above were pAD43-25, pAD123, pMK3, pMK4, and pHCMC02, and the following were respectively obtained:

ATCC 10987/pAD43-25 (EC135/pM.Bce), ATCC 10987/pAD43-25 (TOP10), ATCC 10987/pAD43-25 (EC135), ATCC 10987/pAD123 (EC135/pM.Bce), ATCC 10987/pAD123 (TOP10), ATCC 10987/pAD123 (EC135), ATCC 10987/pMK3 (EC135/pM.Bce), ATCC 10987/pMK3 (TOP10), ATCC 10987/pMK3 (EC135), ATCC 10987/pMK4 (EC135/pM.Bce), ATCC 10987/pMK4 (TOP10), ATCC 10987/pMK4 (EC135), ATCC 10987/pHCMC02 (EC135/pM.Bce), ATCC 10987/pHCMC02 (TOP10), and ATCC 10987/pHCMC02 (EC135);

Using the number of single colonies on the coated plate after transformation, according to the amount of DNA of shuttle plasmids used (since the copy number of pM.Bce was about 5/cell and the copy number of the shuttle plasmid was about 300/cell, the total amount of plasmids added was the amount of DNA of shuttle plasmids), the transformation efficiency was calculated. 4 transformants were picked randomly for DNA verification by extracting plasmids. The experiment was repeated three times and the result employs the average value±the standard deviation.

The transformation efficiency is: the number of single colonies (CFU)×(the volume of recovered solution after transformation/the volume of coated bacterial solution)×the dilution ratio of recovered solution/the amount of shuttle plasmids used in transformation (μg).

Figure 14:
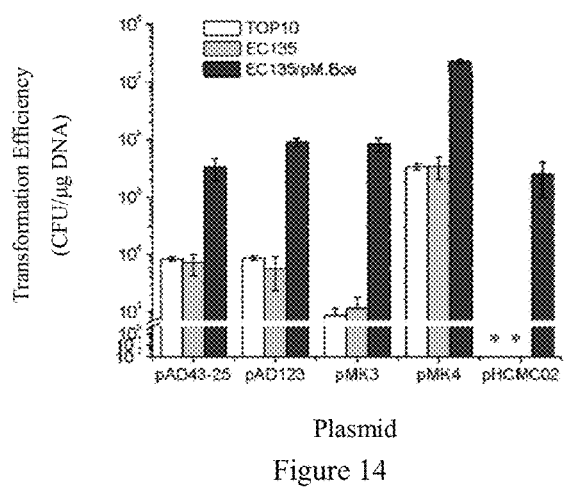
FIG. 14 shows the transformation efficiency of *Bacillus cereus* ATCC 10987 by shuttle plasmids prepared from different hosts (* undetected).

Results are shown in FIG. 14, and it can be seen:

the transformation efficiency for ATCC 10987/pAD43-25 (EC135/pM.Bce) was $3.2\pm1.3\times10^{5}$ CFU/μg DNA;

the transformation efficiency for ATCC 10987/pAD43-25 (TOP10) was $8.3\pm0.7\times10^{3}$ CFU/μg DNA;

the transformation efficiency for ATCC 10987/pAD43-25 (EC135) was $7.1\pm2.9\times10^{3}$ CFU/μg DNA;

the transformation efficiency for ATCC 10987/pAD123 (EC135/pM.Bce) was 9.0±1.4×10$^5$CFU/μg DNA;

the transformation efficiency for ATCC 10987/pAD123 (TOP10) was 8.7±0.8×10$^3$CFU/μg DNA;

the transformation efficiency for ATCC 10987/pAD123 (EC135) was 5.7±3.3×10$^3$CFU/μg DNA;

the transformation efficiency for ATCC 10987/pMK3 (EC135/pM.Bce) was 8.4±2.2×10$^5$CFU/μg DNA;

the transformation efficiency for ATCC 10987/pMK3 (TOP10) was 8.7±2.7×10$^2$CFU/μg DNA; the transformation efficiency for ATCC 10987/pMK3 (EC135) was 1.2±0.6×10$^3$CFU/μg DNA;

the transformation efficiency for ATCC 10987/pMK4 (EC135/pM.Bce) was 2.3±0.2×10$^7$CFU/μg DNA;

the transformation efficiency for ATCC 10987/pMK4 (TOP10) was 3.3±0.4×10$^5$CFU/μg DNA;

the transformation efficiency for ATCC 10987/pMK4 (EC135) was 3.5±1.4×10$^5$CFU/μg DNA;

the transformation efficiency for ATCC 10987/pHCMC02 (EC135/pM.Bce) was 2.5±1.5×10$^5$CFU/μg DNA;

the transformation efficiency for ATCC 10987/pHCMC02 (TOP10) was 0; and the transformation efficiency for ATCC 10987/pHCMC02 (EC135) was 0.

It can be seen that the transformation efficiencies of plasmids prepared in EC135/pM.Bce was 10$^2$-10$^3$ times that of the plasmids prepared in TOP10 and EC135.

Plasmids of single colonies for each strain were extracted simultaneously and an electrophoretic or sequencing comparison with a plasmid before transformation was performed, and the result showed an identical size and demonstrated that these strains were positive plasmids in which an exogenous DNA molecule was transferred.

Example 4

The Introduction of an Exogenous DNA Molecule into *Nitrobacter hamburgensis* X14 by Overcoming Restriction Modification Barrier I. The Construction of Recombinant Bacterium Co-Expressing all DNA-Methyltransferase-Encoding Genes of X14

1. The Achievement of DNA-Methyltransferase-Encoding Genes of Strain X14

1) the Prediction of DNA-Methyltransferase-Encoding Genes of Strain X14

Genome-wide sequences of the strain X14 have been disclosed and their GenBank Nos. are CP000319, CP000320, CP000321, and CP000322. There are total 10 putative DNA-methyltransferase-encoding genes on the chromosome, locus tags of these genes are Nham_0569, Nham_0582, Nham_0803, Nham_0842, Nham_1185, Nham_1353, Nham_2515, Nham_3225, Nham_3845, and Nham_4499, respectively.

2) the Verification of DNA-methyltransferase-Encoding Genes of Strain X14

Nham_0569, Nham_0582, Nham_0803, Nham_0842, Nham_1185, Nham_1353, Nham_2515, Nham_3225, Nham_3845, and Nham_4499 were respectively cloned to sites between EcoRI and KpnI, EcoRI and KpnI, NheI and KpnI, NheI and KpnI, EcoRI and KpnI, EcoRI and KpnI, NheI and KpnI, EcoRI and KpnI, NheI and KpnI, and EcoRI and KpnI of a plasmid pBAD43, so as to obtain a plasmid pBAD43 containing Nham_0569, a plasmid pBAD43 containing Nham_0582, a plasmid pBAD43 containing Nham_0803, a plasmid pBAD43 containing Nham_0842, a plasmid pBAD43 containing Nham_1185, a plasmid pBAD43 containing Nham_1353, a plasmid pBAD43 containing Nham_2515, a plasmid pBAD43 containing Nham_3225, a plasmid pBAD43 containing Nham_3845, and a plasmid pBAD43 containing Nham_4499. The aforementioned types of plasmids were respectively transferred into *E. coli* EC135 to obtain recombinant bacteria 1-10.

Plasmids of recombinant bacteria 1-10 were extracted and sent for sequencing in order to verify correctness, and consequently the recombinant bacteria are positive recombinant bacteria.

Dot Hybridization Verification:

After the recombinant bacteria 1-10 verified to be positive were induced to express methyltransferases (arabinose at a final concentration of 0.2% was used and induction was performed at 30° C. for 12 hours), total DNAs were extracted using DNeasy Blood and Tissue Kit (Qiagen) to obtain DNA1-DNA10. DNA1-DNA10 obtained above were boiled for 3 min to be denaturized into single strands, which were subsequently inserted into an ice-water mixture for quenching. EC135/pBAD43 was used as a negative control.

Total DNAs of EC135/pBAD43 and 10 samples DNA1-DNA10 were all spotted onto a Protran BA85 nitrocellulose film (Whatman) at 450 ng, 150 ng, and 50 ng, which was repeated on three films. The films were placed in 5% skim milk powder formulated with TBST (200 mM NaCl, 0.1% Tween20, 50 mM Tris-HCl, pH7.4) after 2 min UV cross-linking, and were blocked at room temperature for 1 hour. Three films were then placed into a hybridization bag and 10 mL 1:10000 diluted rabbit anti-N6 mA serum, 10 mL 1:10000 diluted rabbit anti-N4mC serum, and 10 mL 1:20000 diluted mouse anti-5mC monoclonal antibody, were added, respectively. The films were washed 5 times after incubation for 1 hour at room temperature, and corresponding goat anti-rabbit second antibody or goat anti-mouse second antibody, with a dilution ratio of 1:10000, was added after the films were placed into the hybridization bag. The films were washed 5 times after incubation for 1 hour at room temperature. Solutions A and B (each 0.5 mL) of an ECL reagent were uniformly mixed and evenly dripped on the surfaces of the films. Fluorescence signal was exposed to X-ray films in a dark room.

Figure 15:
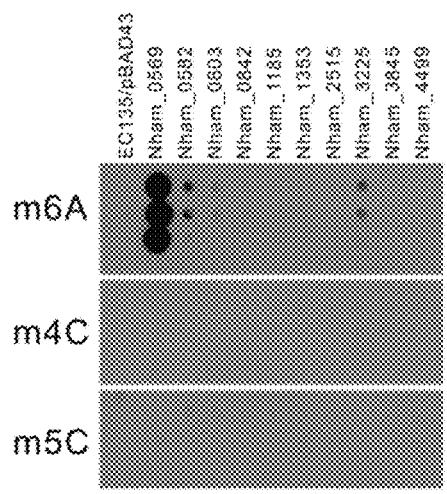
FIG. 15 shows a dot hybridization which detects the activities of DNA methyltransferase of *Nitrobacter hamburgensis* X14.

Results were shown in FIG. 15 (in which m6A/m4C/m5C were results of hybridizations using different antibodies). It can be seen that Nham_0569, Nham_0582, Nham_0803, and Nham_3225 have activities of methylation modification and are DNA methyltransferase genes.

2. The Achievement of Recombinant Bacterium Co-Expressing all DNA-methyltransferase-encoding Genes 1) Construction Using a plasmid pBAD43 containing Nham_0569 (SEQ ID NO: 12), containing Nham_0582 (SEQ ID NO: 13), a plasmid pBAD43 containing Nham_0803 (SEQ ID NO: 14), and a plasmid pBAD43 containing Nham_3225 (SEQ ID NO: 15), as templates respectively, with WB325 and WB585 (having a size of 648 bp) as primers used for Nham_0569, WB586 and WB587 (having a size of 1983 bp) for Nham_0582, WB588 and WB589 (having a size of 1317 bp) for Nham_0803, and WB590 and WB326 (having a size of 1131 bp) for Nham_3225, the sequences of the primers being as shown in Table 1, PCR amplification was performed to obtain 4 PCR products respectively.

The 4 PCR products were respectively recovered by cutting the gel, and equal proportions of the 4 PCR products were mixed and concentrated to a total volume 50 μL to obtain PCR total products.

Figure 16:
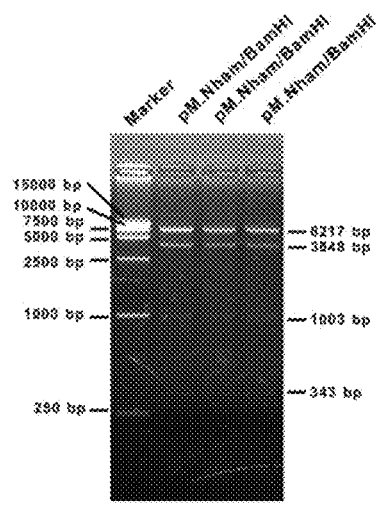
FIG. 16 shows an electrophoretogram of pM.Nham detected by BamHI single cleavage.
Figure 17:
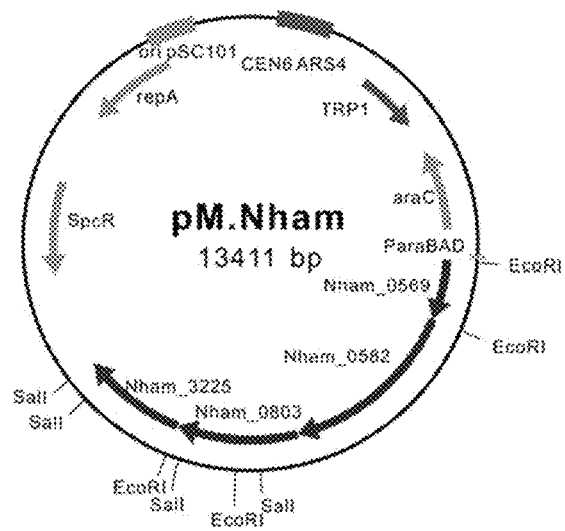
FIG. 17 shows a plasmid map of pM.Nham.

500 ng of plasmid pWYE724 was double-cleaved by EcoRI and SalI, and was mixed with the PCR total products described above after being recovered by cutting, and then by using a lithium acetate transformation method (Methods in Enzymology, 350, 87-96.), *Saccharomyces cerevisiae* DAY414 was transformed. Transformants were screened on a plate of a complete synthetic culture medium without tryptophan added (SC trp-, Beijing FunGenome Co., Ltd.). A single colony was picked into a YPD culture medium, and a yeast plasmid was extracted using a glass bead method (Nucleic Acids Research, 20, 3790). The plasmid was transformed into *E. coli* TOP10, transformants were screened using an LB plate containing 100 μg/mL spectinomycin, and BamHI single cleavage was performed after the plasmid was extracted. A correct recombinant plasmid should generate four bands 8217 bp, 3848 bp, 1003 bp, and 343 bp (as shown in FIG. 16), which was designated as pM.Nham (the structural schematic diagram was shown in FIG. 17), and was sent for sequencing to demonstrate that the result was correct.

pM.Bce was transformed into the strain EC135 obtained in example 1, and cleavage verification was performed according to the method described above. The correct transformant was EC135/pM.Nham, which was a host precisely simulated in a pattern of *Nitrobacter hamburgensis* X14 DNA methylation.

2) Verification

In order to detecting the effectiveness of methylation simulation, methyltransferase genes in EC135 μM.Bam were allowed to be expressed by arabinose induction (inducing at 30° C. for 12 hours using arabinose induction with a final concentration of 0.2%). Total DNAs were extracted and dot hybridization detection was performed using chromosomal DNA of the strain X14 as a control according to the aforementioned method, and the result was that there was no significant difference in the hybridization between EC135/pM.Nham and the strain X14, which demonstrated that methyltransferases were all expressed, and which demonstrated that EC135/pM.Nham was a recombinant bacterium co-expressing all DNA-methyltransferase-encoding genes.

II. The Introduction of Shuttle Plasmid into a Target Bacterium by Overcoming Restriction Modification Barrier The particular method for constructing a plasmid pBBR1-MCS5P$_{Nham\_3450}$-GFP was: Using WB654 and WB655 as primers and the genome of the strain X14 as the template, a gene Nham_3450 promoter fragment 216 bp was subject to amplification. Using WB656 and WB650 as primers and pAD123 as the template, gene GFP 717 bp was subject to amplification; the two PCR products were recovered by cutting the gel and were selected (1 μL each) as templates, and PCR was performed again using WB654 and WB650 as primers to obtain a PCR product of 933 bp, which was cloned into sites SalI and PstI of a plasmid pBBR1-MCS5 (Four new derivatives of the broad-host-range cloning vector pBBR1MCS, carrying different antibiotic-resistance cassettes. Kovach, Michael E. Elzer, Philip H. Steven Hill, D. Robertson, Gregory T. Farris, Michael A. Roop Ii, R. Martin Peterson, Kenneth M. 1995, Gene 166 (1): 175-176, publically available from Institute Of Microbiology Chinese Academy of Sciences). Sequencing verification was performed.

The plasmid pBBR1-MCS5-P$_{Nham\_3450}$-GFP was a broad-host-range plasmid containing green fluorescent protein encoding gene operated by Nham_3450, which was transferred into EC135/pM.Nham, subjected to plasmid extraction after arabinose induction, and transformed the strain X14, and the method for transforming the strain X14 was as follows: The strain was cultured in a DSM756a culture medium (1.5 g yeast extract, 1.5 g peptone, 2 g NaNO$_2$, 0.55 g sodium pyruvate, 1 mL trace element solution (33.8 mg MnSO$_4$.H$_2$O, 49.4 mg H$_3$BO$_3$, 43.1 mg ZnSO$_4$.7H$_2$O, 37.1 mg (NH$_4$)$_6$Mo$_7$O$_{24}$, 97.3 mg FeSO$_4$.7H$_2$O and 25 mg CuSO$_4$.5H$_2$O in 1 L deionized water) and 100 mL stock solution (0.07 g CaCO$_3$, 5 g NaCl, 0.5 g MgSO$_4$.7H$_2$O, 1.5 g KH$_2$PO$_4$ in 1 L deionized water) in 1 L deionized water, pH 7.4)) until OD$_{600}$ was 0.1, was subject to ice bath 10 min, and was centrifuged at 4° C. in 8000 rpm for 10 min to collect bacteria, which were washed with 10% precooled glycerol for 4 times and re-suspended in 10% glycerol in ¹⁄₁₀₀₀ of the volume of the original culture. 90 μL cells were selected and uniformly mixed with 150 ng plasmids, the mixture was added to a 1 mm electroporation cup with 1200V electric shock once (electroporator ECM399). The cells were washed into 100 mL 756a culture medium, were recovered at 28° C. for 1 day, and then were added to gentamycin with a final concentration of 20 μg/mL for further recovery for 1 day. A recovered mixture was trans-inoculated to a fresh 756a culture medium containing 20 μg/mL gentamycin at a volume ratio of ¹⁄₁₀₀. After OD$_{600}$ of the culture medium was 0.1, trans-inoculation was performed once more using the same method, until the bacteria were grown to the extent that OD$_{600}$ was 0.1, so as to obtain X14/pBBR1-MCS5-P$_{Nham\_3450}$-GFP (EC135/pM.Nham);

10 μL, culture broths of X14/pBBR1-MCS5-P$_{Nham\_3450}$-GFP (EC135/pM.Nham) were respectively selected, and were placed under a fluorescence microscope for observation after smearing, with X14 as a control.

Figure 18:
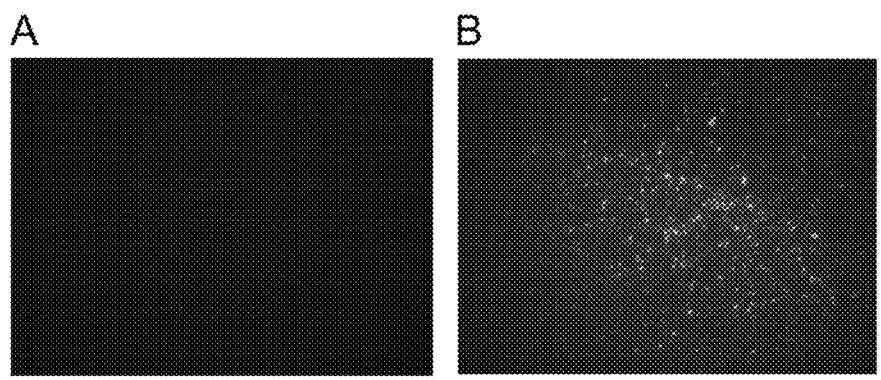
FIG. 18 shows the expression of green fluorescent protein in *Nitrobacter hamburgensis* X14.

Results were shown in FIG. 18, in which A was X14 and B was X14/pBBR1-MCS5-P$_{Nham\_3450}$-GFP (EC135/pM.Nham). It can be seen that bacteria X14/pBBR1-MCS5-P$_{Nham\_3450}$-GFP (EC135/pM.Nham) emits green fluorescence under 488 nm excitation light and untransformed bacteria do not have fluorescence.

It was demonstrated that an exogenous gene has been transferred.

10 mL×14/pBBR1-MCS5-P$_{Nham\_3450}$-GFP (EC135/pM.Nham) bacterial solution was selected, and total DNAs were extracted using a bacterial DNA extraction kit (DP302-02, Tiangen CO.). Then, 5 μL DNA transformed *E. coli* TOP10 was selected, gentamycin-resistant transformants were screened, and the extracted plasmid was verified to have an identical size (5701 bp) to that of the original plasmid pBBR1-MCS5-P$_{Nham\_3450}$-GFP, which demonstrated that the exogenous DNA molecule pBBR1-MCS5-P$_{Nham\_3450}$-GFP in X14/pBBR1-MCS5-P$_{Nham\_3450}$-GFP (EC135/pM.Nham) did not have any loss and was completely transferred into X14 by overcoming the restriction modification barrier.

In contrast, Carsiotis, M. et al. reported (Genetic engineering of enhanced microbial nitrification. Carsiotis, M. and Khanna, S. US Environmental Protection Agency, Risk Reduction Engineering Laboratory. 1989) that plasmid DNA extracted from a normal host of *E. coli* failed to achieve genetic transformation to the strain X14. Consequently, the method reported herein has great advantages.

What is claimed is:

1. A method for introducing a methylated exogenous DNA molecule into a target bacterium, the method comprising the steps of:
   a) providing an original *E. coli* strain having a deficient recA gene;
   b) repairing the deficient recA gene and knocking out the dcm gene and the dam gene of the original *E. coli* strain to obtain a modified *E. coli* strain;
   c) co-expressing in the modified *E. coli* strain all putative DNA-methyltransferase-encoding genes encoding functional DNA methyltransferases in the genome of the target bacterium to obtain a recombinant *E. coli* bacterium A which shows the same DNA methylation pattern as that of the target bacterium;
   d) introducing an exogenous DNA molecule into said recombinant *E. coli* bacterium A for in vivo modification to obtain a methylated exogenous DNA molecule and extracting the methylated exogenous DNA molecule to obtain an extracted methylated exogenous DNA molecule; and
   e) introducing said extracted methylated exogenous DNA molecule into said target bacterium,
   wherein the target bacterium is not an *E. coli* strain.

2. The method according to claim 1, wherein step c) is accomplished by introducing a recombinant expression vector carrying all of the putative DNA-methyltransferase-encoding genes into said modified *E. coli* strain; and step d) is accomplished by the substeps of:
   A) introducing said exogenous DNA molecule into said recombinant *E. coli* bacterium A to obtain a recombinant *E. coli* bacterium B;
   B) inducing and culturing said recombinant *E. coli* bacterium B to obtain an induced recombinant *E. coli* bacterium B; and
   C) extracting the DNA of said induced recombinant *E. coli* bacterium B to obtain said extracted methylated exogenous DNA molecule.

3. The method according to claim 2, wherein in substep B), said inducing is inducing by temperature or by arabinose, IPTG, xylose, or rhamnose.

4. The method according to claim 3, wherein substep B) is accomplished by culturing the recombinant *E. coli* bacterium B in a liquid culture medium containing arabinose at a final concentration of 0.2% by mass, the culturing being performed at a temperature of 25° C.-37° C. for 3-24 hours.

5. The method according to claim 1, wherein said target bacterium is *Bacillus amyloliquefaciens* TA208, *Bacillus cereus* ATCC 10987, or *Nitrobacter hamburgensis* X14; and said modified *E. coli* strain is *Escherichia coli* EC135, deposited as strain CGMCC No. 5925.

6. The method according to claim 1, wherein said exogenous DNA molecule is an exogenous plasmid DNA molecule.

7. The method according to claim 5, wherein said all putative DNA-methyltransferase-encoding genes encoding functional DNA methyltransferases of said *Bacillus amyloliquefaciens* TA208 are encoded by SEQ ID NO: 2, SEQ ID NO: 3, SEQ ID NO: 4, and SEQ ID NO: 5;
   said all putative DNA-methyltransferase-encoding genes encoding functional DNA methyltransferases of said *Bacillus cereus* ATCC 10987 are encoded by SEQ ID NO: 6, SEQ ID NO: 7, SEQ ID NO: 8, SEQ ID NO: 9, SEQ ID NO: 10, and SEQ ID NO: 11; or
   said all putative DNA-methyltransferase-encoding genes encoding functional DNA methyltransferases of said *Nitrobacter hamburgensis* X14 are encoded by SEQ ID NO: 12, SEQ ID NO: 13, SEQ ID NO: 14, and SEQ ID NO: 15.

8. The method according to claim 1, further comprising determining said all putative DNA-methyltransferase-encoding genes encoding functional DNA methyltransferases in the genome of the target bacterium as follows:
   (a) determining putative genes encoding DNA methyltransferases in a target bacterium by homologous sequence alignment;
   (b) introducing each putative gene encoding DNA methyltransferases into *E. coli*; and
   (c) preparing genome DNAs of the aforementioned *E. coli* and detecting whether DNAs have been methylated.

9. The method according to claim 4, wherein the culturing is performed at a temperature of 30° C. for 12 hours.

10. The method according to claim 1, wherein said target bacterium is an *Eubacterium* or *Archaebacterium* containing a restriction modification system.

* * * * *

SEQUENCE LISTING

<160> NUMBER OF SEQ ID NOS: 15

<210> SEQ ID NO 1
<211> LENGTH: 8309
<212> TYPE: DNA
<213> ORGANISM: Artificial sequence
<220> FEATURE:
<223> OTHER INFORMATION: Synthetic polynucleotide

<400> SEQUENCE: 1

| | | | | | |
|---|---|---|---|---|---|
| cctgatatag | gcgccagcaa | ccgcacctgt | ggcgccggtg | atgccggcca | cgatgcgtcc | 60 |
| ggcgtagagg | atctgctcat | gtttgacagc | ttatcatcga | tacacggaaa | tgttgaatac | 120 |
| tcatactctt | cctttttcaa | tattattgaa | gcatttatca | gggttattgt | ctcatgagcg | 180 |
| gatacatatt | tgaatgtatt | tagaaaaata | aacaaatagg | ggttccgcgc | acatttcccc | 240 |
| gaaaagtgcc | acctgggtcc | ttttcatcac | gtgctataaa | aataattata | atttaaattt | 300 |
| tttaatataa | atatataaat | taaaaataga | aagtaaaaaa | agaaattaaa | gaaaaaatag | 360 |
| tttttgtttt | ccgaagatgt | aaaagactct | aggggatcg | ccaacaaata | ctaccttta | 420 |
| tcttgctctt | cctgctctca | ggtattaatg | ccgaattgtt | tcatcttgtc | tgtgtagaag | 480 |
| accacacacg | aaaatcctgt | gattttacat | tttacttatc | gttaatcgaa | tgtatatcta | 540 |
| tttaatctgc | ttttcttgtc | taataaatat | atatgtaaag | tacgcttttt | gttgaaattt | 600 |
| tttaaacctt | tgtttatttt | tttttcttca | ttccgtaact | cttctaccttt | ctttattac | 660 |
| tttctaaaat | ccaaatacaa | aacataaaaa | taaataaaca | cagagtaaat | tcccaaatta | 720 |
| ttccatcatt | aaaagatacg | aggcgcgtgt | aagttacagg | caagcgatcc | gtctaagaaa | 780 |
| ccattattat | catgacatta | acctataaaa | ataggcgtat | cacgaggccc | tttcgtctcg | 840 |
| cgcgtttcgg | tgatgacggt | gaaaacctct | gacacatgca | gctcccggag | acggtcacag | 900 |
| cttgtctgta | agcggatgcc | gggagcagac | aagcccgtca | gggcgcgtca | gcgggtgttg | 960 |
| gcgggtgtcg | gggctggctt | aactatgcgg | catcagagca | gattgtactg | agagtgcacc | 1020 |
| atagatcacg | acattactat | atatataata | taggaagcat | ttaatagaac | agcatcgtaa | 1080 |
| tatatgtgta | ctttgcagtt | atgacgccag | atggcagtag | tggaagatat | tctttattga | 1140 |
| aaaatagctt | gtcaccttac | gtacaatctt | gatccggagc | ttttctttt | ttgccgatta | 1200 |
| agaattaatt | cggtcgaaaa | aagaaaagga | gagggccaag | agggagggca | ttggtgacta | 1260 |
| ttgagcacgt | gagtatacgt | gattaagcac | acaaaggcag | cttggagtat | gtctgttatt | 1320 |
| aatttcacag | gtagttctgg | tccattggtg | aaagtttgcg | gcttgcagag | cacagaggcc | 1380 |
| gcagaatgtg | ctctagattc | cgatgctgac | ttgctgggta | ttatatgtgt | gcccaataga | 1440 |
| aagagaacaa | ttgacccggt | tattgcaagg | aaaatttcaa | gtcttgtaaa | agcatataaa | 1500 |
| aatagttcag | gcactccgaa | atacttggtt | ggcgtgtttc | gtaatcaacc | taaggaggat | 1560 |
| gttttggctc | tggtcaatga | ttacggcatt | gatatcgtcc | aactgcatgg | agatgagtcg | 1620 |
| tggcaagaat | accaagagtt | cctcggtttg | ccagttatta | aaagactcgt | atttccaaaa | 1680 |
| gactgcaaca | tactactcag | tgcagcttca | cagaaacctc | attcgtttat | tcccttgttt | 1740 |
| gattcagaag | caggtgggac | aggtgaactt | ttggattgga | actcgatttc | tgactgggtt | 1800 |
| ggaaggcaag | agagccccga | aagcttacat | tttatgttag | ctggtggact | gacgccagaa | 1860 |
| aatgttggtg | atgcgcttag | attaaatggc | gttattggtg | ttgatgtaag | cggaggtgtg | 1920 |
| gagacaaatg | tgtaaaaga | ctctaacaaa | atagcaaatt | tcgtcaaaaa | tgctaagaaa | 1980 |
| taggttatta | ctgagtagta | tttatttaag | tattgtttgt | gcacttgccg | tctcttatgc | 2040 |

```
cggtgtgaaa taccgcacag atgcgtaagg agaaaatacc gcatcaggaa attgtaagcg    2100
ttaatatttt gttaaaattc gcgttaaatt tttgttaaat cagctcattt tttaaccaat    2160
aggccgaaat cggcaaaatc ccttataaat caaaagaata gaccgagata gggttgagtg    2220
ttgttatcga tgcataatgt gcctgtcaaa tggacgaagc agggattctg caaccctat    2280 gctactccgt caagccgtca attgtctgat tcgttaccaa ttatgacaac ttgacggcta    2340
catcattcac tttttcttca caaccggcac ggaactcgct cgggctggcc ccggtgcatt    2400
ttttaaatac ccgcgagaaa tagagttgat cgtcaaaacc aacattgcga ccgacggtgg    2460
cgataggcat ccggggtggtg ctcaaaagca gcttcgcctg gctgatacgt tggtcctcgc    2520
gccagcttaa gacgctaatc cctaactgct ggcggaaaag atgtgacaga cgcgacggcg    2580
acaagcaaac atgctgtgcg acgctggcga tatcaaaatt gctgtctgcc aggtgatcgc    2640
tgatgtactg acaagcctcg cgtacccgat tatccatcgg tggatggagc gactcgttaa    2700
tcgcttccat gcgccgcagt aacaattgct caagcagatt tatcgccagc agctccgaat    2760
agcgcccttc cccttgcccg gcgttaatga tttgcccaaa caggtcgctg aaatgcggct    2820
ggtgcgcttc atccgggcga agaaccccg tattggcaaa tattgacggc cagttaagcc    2880
attcatgcca gtaggcgcgc ggacgaaagt aaacccactg gtgataccat tcgcgagcct    2940
ccggatgacg accgtagtga tgaatctctc ctggcgggaa cagcaaaata tcacccggtc    3000
ggcaaacaaa ttctcgtccc tgattttca ccacccctg accgcgaatg gtgagattga    3060
gaatataacc tttcattccc agcggtcggt cgataaaaaa atcgagataa ccgttggcct    3120
caatcggcgt taaacccgcc accagatggg cattaaacga gtatcccggc agcagggat    3180 cattttgcgc ttcagccata cttttcatac tcccgccatt cagagaagaa accaattgtc    3240
catattgcat cagacattgc cgtcactgcg tcttttactg gctcttctcg ctaaccaaac    3300 cggtaaccccc gcttattaaa agcattctgt aacaaagcgg gaccaaagcc atgacaaaaa    3360
cgcgtaacaa aagtgtctat aatcacggca gaaaagtcca cattgattat ttgcacggcg    3420
tcacactttg ctatgccata gcatttttat ccataagatt agcggatcct acctgacgct    3480
ttttatcgca actctctact gtttctccat acccgttttt ttgggctagc aggaggaatt    3540
caccatggta cccgggggatc ctctagagtc gacctgcagg catgcaagct tggctgtttt    3600
ggcggatgag agaagatttt cagcctgata cagattaaat cagaacgcag aagcggtctg    3660
ataaaacaga atttgcctgg cggcagtagc gcggtggtcc cacctgaccc catgccgaac    3720
tcagaagtga acgccgtag cgccgatggt agtgtgggg ctccccatgc gagagtaggg    3780
aactgccagg catcaaataa aacgaaaggc tcagtcgaaa gactgggcct ttcgttttat    3840
ctgttgtttg tcggtgaacg ctctcctgag taggacaaat ccgccgggag cggatttgaa    3900
cgttgcgaag caacggcccg gagggtggcg ggcaggacgc ccgccataaa ctgccaggca    3960
tcaaattaag cagaaggcca tcctgacgga tggcctttt gcgtttctac aaactctttt    4020 gtttatttt ctaaatacat tcaaatatgt atccgctcat gagacaataa ccctagctta    4080
ctggccgtcg ttttacaacg tcgtgactgg gaaaaccctg gcgttaccca acttaatcgc    4140
cttgcagcac atccccctt cgccagctgg cgtaatagcg aagaggcccg caccgatcgc    4200
ccttcccaac agttgcgcag cctgaatggc gaatggcgcc tgatgcggta ttttctcctt    4260
acgcatctgt gcggtatttc acaccgcata tggtgcactc tcagtacaat ctgctctgat    4320
gccgcatagt taagccagcc ccgacacccg ccaacacccg ctgacgagct tagtaaagcc    4380
```

```
ctcgctagat tttaatgcgg atgttgcgat tacttcgcca actattgcga taacaagaaa    4440
aagccagcct ttcatgatat atctcccaat ttgtgtaggg cttattatgc acgcttaaaa    4500
ataataaaag cagacttgac ctgatagttt ggctgtgagc aattatgtgc ttagtgcatc    4560
taacgcttga gttaagccgc gccgcgaagc ggcgtcggct tgaacgaatt gttagacatt    4620
atttgccgac taccttggtg atctcgcctt tcacgtagtg acaaattct  tccaactgat    4680 ctgcgcgcga ggccaagcga tcttcttctt gtccaagata agcctgtcta gcttcacgta    4740
tgacgggctg atactgggcc ggcaggcgct ccattgccca gtcggcagcg acctccttcg    4800
gcgcgatttt gccggttact cgctgtacc  aaatgcggga caacgtaagc actacatttc    4860
gctcatcgcc agcccagtcg ggcggcgagt tccatagcgt taaggtttca tttagcgcct    4920
caaatagatc ctgttcagga accggatcaa agagttcctc cgccgctgga cctaccaagg    4980
caacgctatg ttctcttgct tttgtcagca agatagccag atcaatgtcg atcgtggctg    5040
gctcgaagat acctgcaaga atgtcattgc gctgccattc tccaaattgc agttcgcgct    5100
tagctggata acgccacgga atgatgtcgt cgtgcacaac aatggtgact tctacagcgc    5160
ggagaatctc gctctctcca ggggaagccg aagtttccaa aaggtcgttg atcaaagctc    5220
gccgcgttgt ttcatcaagc cttacggtca ccgtaaccag caaatcaata tcactgtgtg    5280
gcttcaggcc gccatccact gcggagccgt acaaatgtac ggccagcaac gtcggttcga    5340
gatggcgctc gatgacgcca actacctctg atagttgagt cgatacttcg gcgatcaccg    5400
cttccctcat gatgtttaac tttgttttag ggcgactgcc ctgctgcgta acatcgttgc    5460
tgctccataa catcaaacat cgacccacgg cgtaacgcgc ttgctgcttg gatgcccgag    5520
gcatagactg taccccaaaa aaacagtcat aacaagccat gaaaaccgcc actgcgccgt    5580
taccaccgct gcgttcggtc aaggttctgg accagttgcg tgagcgcata cgctacttgc    5640
attacagctt acgaaccgaa caggcttatg tccactgggt tcgtgccttc atccgtttcc    5700
acggtgtgcg tcacccggca accttgggca gcagcgaagt cgaggcattt ctgtcctggc    5760
tggcgaacga gcgcaaggtt tcggtctcca cgcatcgtca ggcattggcg gccttgctgt    5820
tcttctacgg caaggtgctg tgcacggatc tgccctggct tcaggagatc ggaagacctc    5880
ggccgtcgcg gcgcttgccg gtggtgctga ccccggatga agtaattccc acgggttttg    5940
ctgcccgcaa acgggctgtt ctggtgttgc tagtttgtta tcagaatcgc agatccggct    6000
tcaggtttgc cggctgaaag cgctatttct tccagaattg ccatgatttt ttccccacgg    6060
gaggcgtcac tggctcccgt gttgtcggca gctttgattc gataagcagc atcgcctgtt    6120
tcaggctgtc tatgtgtgac tgttgagctg taacaagttg tctcaggtgt tcaatttcat    6180
gttctagttg cttttgttta ctggtttcac ctgttctatt aggtgttaca tgctgttcat    6240
ctgttacatt gtcgatctgt tcatggtgaa cagctttgaa tgcaccaaaa actcgtaaaa    6300
gctctgatgt atctatcttt tttacaccgt tttcatctgt gcatatggac agttttccct    6360
ttgatatgta acggtgaaca gttgttctac ttttgtttgt tagtcttgat gcttcactga    6420
tagatacaag agccataaga acctcagatc cttccgtatt tagccagtat gttctctagt    6480
gtggttcgtt gttttgcgt  gagccatgag aacgaaccat tgagatcata cttactttgc    6540
atgtcactca aaaattttgc ctcaaaactg gtgagctgaa tttttgcagt taaagcatcg    6600
tgtagtgttt ttcttagtcc gttatgtagg taggaatctg atgtaatggt tgttggtatt    6660
ttgtcaccat tcatttttat ctggttgttc tcaagttcgg ttacgagatc catttgtcta    6720
tctagttcaa cttggaaaat caacgtatca gtcgggcggc ctcgcttatc aaccaccaat    6780
```

```
ttcatattgc tgtaagtgtt taaatcttta cttattggtt tcaaaaccca ttggttaagc    6840
cttttaaact catggtagtt attttcaagc attaacatga acttaaattc atcaaggcta    6900
atctctatat ttgccttgtg agttttcttt tgtgttagtt cttttaataa ccactcataa    6960
atcctcatag agtatttgtt ttcaaaagac ttaacatgtt ccagattata ttttatgaat    7020 tttttaact ggaaaagata aggcaatatc tcttcactaa aaactaattc taatttttcg    7080
cttgagaact tggcatagtt tgtccactgg aaaatctcaa agcctttaac caaaggattc    7140
ctgatttcca cagttctcgt catcagctct ctggttgctt tagctaatac accataagca    7200
ttttccctac tgatgttcat catctgagcg tattggttat aagtgaacga taccgtccgt    7260
tctttccttg tagggttttc aatcgtgggg ttgagtagtg ccacacagca taaaattagc    7320
ttggtttcat gctccgttaa gtcatagcga ctaatcgcta gttcatttgc tttgaaaaca    7380
actaattcag acatacatct caattggtct aggtgatttt aatcactata ccaattgaga    7440
tgggctagtc aatgataatt actagtcctt ttcctttgag ttgtgggtat ctgtaaattc    7500
tgctagacct ttgctggaaa acttgtaaat tctgctagac cctctgtaaa ttccgctaga    7560
cctttgtgtg ttttttttgt ttatattcaa gtggttataa tttatagaat aaagaaagaa    7620 taaaaaaga taaaaagaat agatcccagc cctgtgtata actcactact ttagtcagtt    7680
ccgcagtatt acaaaaggat gtcgcaaacg ctgtttgctc ctctacaaaa cagaccttaa    7740
aaccctaaag gcttaagtag caccctcgca agctcgggca aatcgctgaa tattccttt    7800 gtctccgacc atcaggcacc tgagtcgctg tcttttcgt gacattcagt tcgctgcgct     7860
cacggctctg gcagtgaatg ggggtaaatg gcactacagg cgccttttat ggattcatgc    7920
aaggaaacta cccataatac aagaaaagcc cgtcacgggc ttctcagggc gttttatggc    7980
gggtctgcta tgtggtgcta tctgactttt tgctgttcag cagttcctgc cctctgattt    8040
tccagtctga ccacttcgga ttatcccgtg acaggtcatt cagactggct aatgcaccca    8100
gtaaggcagc ggtatcatca acaggcttac ccgtcttact gtcgggaatt aattcgttgg    8160
ccgattcatt aatgcagctg gcacgacagg tttcccgact ggaaagcggg cagtgagcgc    8220
aacgcaatta atgtgagtta gctcactcat taggcacccc aggctttaca ctttatgctt    8280
ccggctcgta tgttgtgtgg aattgtgag                                     8309
```

<210> SEQ ID NO 2
<211> LENGTH: 840
<212> TYPE: DNA
<213> ORGANISM: Artificial sequence
<220> FEATURE:
<223> OTHER INFORMATION: Synthetic polynucleotide

<400> SEQUENCE: 2

```
ttggaactaa acaaaataca taataatgat tgcgtacaat tcatgaaaga gaatattggt      60
gattgcacta tcgacttaac agtgacttct cctccttatg atgacctaag gaattacaat     120
ggatattcat ttaactttga ggaaactgct caagaattgt atagggtgac aaaagagggc     180
ggagtcgttg tttgggtagt agggataaa acacataaag gttccgagac agggtcaagt      240
tttagacaag ctttatactt taagagttg ggctttaacc tacatgacac aatgattat       300 gaaaaagaca gtatcagctt tccagataag aatagatatt tcagatttt tgagtatatg     360 tttatttttt cgaaaggcaa gccaaaaaca atcaatctat tagcagacag gaaaaataaa     420
tggtacaacg gcaagaaaca cataaaagga cattacagaa aaatggacgg cgaaaaagta     480
```

```
cgacatcata aacagaactt actaaaggag ttcggtgtga ggttcaacat ttggaggata      540
ccgaacggtc atcaaaaatc aacactagac aagatcgctt ttcaacatcc ggcaatattt      600
ccagaaaagc ttgctgaaga tcacattctc tcttggtcaa atgaaggaga catagtattt      660
gatccgttta tgggaagtgg aacaactgca aagatggcag ctttaaataa ccgtaaatac      720
ataggaacag aaattagtaa agagtattgt gatattgcaa atgaacgatt aaagaattat      780
ataattttgc ataaaagaat ggagggcaaa gggtatcgat tacctcaagt acatagttga      840

<210> SEQ ID NO 3
<211> LENGTH: 1512
<212> TYPE: DNA
<213> ORGANISM: Artificial sequence
<220> FEATURE:
<223> OTHER INFORMATION: Synthetic polynucleotide

<400> SEQUENCE: 3
ttgaataaac tacgagtaat gagtcttttt agtggaatcg gtgcgtttga agctgcacta       60
agaaacattg gggttgaata tgaactggtt ggctttagtg aaattgataa atatgctatt      120
aagtcatatt gtgcgattca caacgttgat gagcaatcaa attttggtga tgtaagcaag      180
attgataaga aaaaactgcc tgaatttgat cttttagttg gaggatctcc ttgtcaaagc      240
tttagcgtag ccggttatcg gaaagggttc gaagatacta gagggacatt gttttttcaa      300
tatatagata ccttaaaaga gaagaagccg cggtattttg tttttgaaaa tgttaaaggg      360
ttgatcaatc atgataaagg aaatacatta atattatgg ctgaatcttt tagtgaagtt       420
gggtacagaa ttgacttaga gctacttaat tcaaaatttt tcaatgttcc tcagaatcgt      480
gagcgtatat acataattgg agttcgtgag gatttaattg aaaatgacga atggattgtc      540
gaaaagggaa ggaacgatgt tttaagtaag ggaaaaaaga gattaaaaga attaaatata      600 aaagtttca attttaaatg gtctgcacaa gatattgttg aaagagatt gcgagaaatt       660 cttgaggaat atgtagatga gaagtattac ttaagcgaag aaaaaacatc taaactgatt      720
gaacaaattg aaaaaccaaa agaaaaagat gtggtgtttg ttggtggcat taacgtagga      780
aagaggtggc tgaataacgg aaaaacatat tccagaaact ttaaacaagg caatagagtc      840
tatgattcaa atggcattgc aacaactttg acatcccaat cggtaggtgg tctcggaggg      900
cagacttcgc tatacaaagt ggaagacccg atcatgattg tcacattga tctaaaagga       960 catgatgcaa ttaaaagagt gtactcgcct gatggggtgt caccaacatt aacaactatg     1020
ggaggaggtc atagagaacc taaaattgct gttgagtatg ttggtaatat taatccttca     1080
ggagaaggaa tgaatggtca ggtttacaat tcaaatgggc taagttcaac tttaacaaca     1140
aataagggtg aaggggtgaa aatttctgtg ccaaaccctg aaataagacc cgtcttaact     1200
ccagaaaggg aagaaaaaag acaaaatggc agacgcttta agaagacga tgaaccggcc      1260 ttcactgtta atacaattga tcgtcatggt gtagcaattg gcgaataccc aaaatacaga     1320
attagaaagc tcactccatt agaatgttgg agactgcaag catttgatga agaagatttt     1380
gagaaagcct tatcagtggg aattagtaat tcgcagttgt acaagcaagc cggcaattca     1440
attactgtaa ctgtacttga gtcaatattc aaggaattaa tacatacata cgataataaa     1500
gaatctgaat aa                                                        1512

<210> SEQ ID NO 4
<211> LENGTH: 1794
<212> TYPE: DNA
<213> ORGANISM: Artificial sequence
```

<220> FEATURE:
<223> OTHER INFORMATION: Synthetic polynucleotide

<400> SEQUENCE: 4

| | | | | | |
|---|---|---|---|---|---|
| atgaacagca | ataataagag | atttaaactg | gttgatttat | ttgctggtgc | tggaggtcta | 60 |
| agcaaaggat | ttgagcaaac | tggctgcttt | gaaacaattg | gagcggtaga | aataaatcaa | 120 |
| gcagctattg | aaacttatgt | ttataaccac | ggcggaaaca | gagacattat | tattaggccg | 180 |
| gacgaaagtg | ataccagtga | cattagtaaa | atcgacttcc | gtaaatggaa | gaagagcaaa | 240 |
| aacattgatc | ctaatttgtt | aacaattatt | ggcggaccte | cttgtcaagg | attttccaat | 300 |
| gctaataggc | agaaaaatta | tctgatatca | ggaataatc | agcttgttat | agagtttttt | 360 |
| cgtgctattg | atgagatccg | gccagctgca | tttcttatgg | agaatgtgcc | atcgatgaac | 420 |
| tcagataaac | ataaattttt | catcacaaaa | catttagata | attcgcgctt | tgcatatagc | 480 |
| tctttagaac | atttaacttg | cttatttaat | acatcaaaag | aaaagttgat | tgaaaataag | 540 |
| ttttaatgg | atgataagat | aattctaatg | gagtcagttg | aaatatcact | aagtcatatt | 600 |
| tggagaaaaa | tcatcgatgg | ttcaactccc | cctaaaccaa | taattgggga | tcataactac | 660 |
| ttatcccgct | tgaaaagtat | atcaaaaaaa | attataaaga | cagaaggtaa | tcctagcttg | 720 |
| tcactaaagg | aaaaaaaaga | tattattcga | attattgagt | tgattaatca | acaactaaaa | 780 |
| accttccaag | cagatggaga | tcacctaagc | actaaagata | tagtttctcg | tggaaaagca | 840 |
| gcactccaat | tgctgcttga | ggattttgag | gaatttgata | aatgcgctaa | aaaagatatc | 900 |
| actaacttta | tgagtttaaa | tctaatactg | ttaagaataa | aagaactaaa | tgatgaaaaa | 960 |
| attagatatg | agctttatat | agatgataca | cataaggata | atattaaaat | cattgcaaag | 1020 |
| gtttggtctt | ataatattgt | aaaatatctt | gaaatggcat | tccaccaaat | tggatataat | 1080 |
| actgatttcg | gggtcttaac | agctacagac | tttggcgtac | cacaaataag | aagaaggttt | 1140 |
| atcatccttg | gtgttagaaa | tgatttattt | gagaacagtc | cgaaacttcc | cgatgcgttg | 1200 |
| gtacactcaa | cacctttac | agtaagggat | gcaatacagg | atttagccga | taacgccc | 1260 |
| cttacagata | tggaaaaagc | taaaccatta | gattatatag | aatcagatgc | gcaggcatcg | 1320 |
| cctatgcttc | gatatttcag | aaaagatgct | gataaagggt | tgattgataa | tcatataaat | 1380 |
| actgaaagcc | gtcagctaag | taaaactcgt | tttgaagcaa | tacttcaatt | gaaaggtaaa | 1440 |
| aatttccaca | gtcttaatga | tgagttaaaa | acaacctact | ctgatgtgtc | tagaacacag | 1500 |
| aatacaatct | atttaagact | agactatggc | agtccatctc | ctacagtcgt | taacgtaagg | 1560 |
| aaatcaatgt | ggagtcatcc | agaaaaagct | agagcaataa | gtattcgcga | ggcagcccgt | 1620 |
| ctgcaatcat | ttccagataa | ttttaaattt | agagggacaa | aagatcagca | atatcaacaa | 1680 |
| gtagggaatg | cagttccccc | tttgcttgga | cgtgcagcag | ccgaggcatt | attaaatgct | 1740 |
| atgggtgttg | agcctactat | ctcacttaaa | aatgaattat | tagatttaga | ataa | 1794 |

<210> SEQ ID NO 5
<211> LENGTH: 1272
<212> TYPE: DNA
<213> ORGANISM: Artificial sequence
<220> FEATURE:
<223> OTHER INFORMATION: Synthetic polynucleotide

<400> SEQUENCE: 5

| | | | | | |
|---|---|---|---|---|---|
| ttgcgttttt | tttctgtttt | tgacattgtt | aaaaataaag | cgaatcagtt | agggtatacg | 60 |
| gaaactgaaa | tgtatgctgt | attgaaaaat | tacaatgtga | ataagaagga | tttactcgcc | 120 |

| | |
|---|---|
| tataaagaaa atggagttat tccaacagat aaagtgttga atggaatact tagttatctt | 180 |
| ggaatgacta agtagaatt agaattaaaa ttaggcagga taccggctgg gttagaggat | 240 |
| gtgttcttaa ataacacaaa agaaattgcc aagatcctcg aaaataaaaa tagtgttaaa | 300 |
| ctaaacgaat taattctat tcaagaaatc aaaccttatt tttatactga tcttggaaaa | 360 |
| ttatacaatg gggattgttt agaactgttt aaacaagttc ctgatgaaaa cgtggacact | 420 |
| attttttgctg atccaccatt taaccttgat aaagagtatg atgagggtgt aacagataaa | 480 |
| aattcctta gcggatattt ggattggtat tataaatgga tagacgagtg tatcagagtt | 540 |
| ttaaaaccag gcggttcttt attcatttat aatattccaa aatggaacac ttacctttct | 600 |
| gagtacttaa ataggaaatt gaattttaga aactggataa ctgtagatat gaaatttgga | 660 |
| cttccaattc agaatagatt atatccagca aattacagcc ttttatacta tgtaaaaggt | 720 |
| gataaaccta agacatttaa tgttcaaagg atacctctac aaacttgccc tcattgtggt | 780 |
| agagaaataa aagactatgg cggttacaag aataaaatga acccaaaggg tgtaactctt | 840 |
| tctgatgttt ggtcagatat ttaccctgtt agacatagta gttcaaaaaa tagaaagttc | 900 |
| aatgaattat cagttaaatt acttgatcgt ataataacta tgagtacaaa tgaaggtgac | 960 |
| gttgttttag acccgtttgg aggaagcggt acaacatttg ctgtaagtga atgttaggt | 1020 |
| cgtaaatgga ttggttttga gttggggaat tgtgaaatta tcaaagagag acttaaaaat | 1080 |
| aaagacaaag ataaaaagct gttaggtaaa gtttatgaag aaaaaaacaa gctgttccct | 1140 |
| aatagggtta agaattacg taaaaaaaat ggtttatgga ttgatgatga ttttagacaa | 1200 |
| gaccatgagg gaaattctaa aggtgataaa aaaaacgaaa acaatgacca aatttcatta | 1260 |
| agtctagaat ga | 1272 |

<210> SEQ ID NO 6
<211> LENGTH: 2160
<212> TYPE: DNA
<213> ORGANISM: Artificial sequence
<220> FEATURE:
<223> OTHER INFORMATION: Synthetic polynucleotide

<400> SEQUENCE: 6

| | |
|---|---|
| atgagtaaat tgacacttgg ttccctcttt gatggcagtg gtggttttcc tttgggtggt | 60 |
| ttgctttgtg gcatcgaacc tttatgggca tctgaaattg agccgttttcc tatacgggtt | 120 |
| acgactaaac gtatccctca gatgaagcat tatggagata taaacaaatt aaatggtgcg | 180 |
| gagcttccgc ctgtagatat cataaccttc ggctctccat gcacggatat gagtgtggcg | 240 |
| ggtaaaagag ctggtttgga cggagagcaa tccgtccttt tttatgaagc aatccgaatt | 300 |
| attaaggaaa tgaggtgtaa gaccaatgga caatatccaa ggtacgcagt ctgggaaaat | 360 |
| gtccccggtg cattctcgtc gaataaagga gaagacttca agcagtcct cgaaacggtc | 420 |
| atcagtgtca agaaccgaa tacctcggtg cctttacctg aaaaaggacg atggccatac | 480 |
| gctgacatct atatgggaga cggatggagc gtggcttacc gaactatcga tgcgcaatat | 540 |
| ttcggagtcc cccaacgtcg tcgtagaatc taccttgtcg cagattttgc agacggatgt | 600 |
| gccggagaaa tactatttga gtccgaaggc ttgtcaaggg attttacgcc gagcggcagc | 660 |
| ccgtggcaaa gaactgccgg aaatgctaaa aaccgctctg aaaaacagg cgatagcata | 720 |
| acttgcctaa atgaccaagg cggaagagtg atgtctgttt cgaaggatat tacagcaaca | 780 |
| cttcgagcag aggaacatgg acatcagcct tgcgtaatgc agtcaagcgg attttgtact | 840 |
| gaacacagtg ccaagagcag aagtgtagga tatgaggaag aacgttcccc tacacttaga | 900 |

```
acaggtgttg tcccaggtgc agtcatgtcc tttgaaccgg gtgctgcttc tcgagttggt    960
ggccatactg acgaaaactt aagtggatca cttcgtgcaa acatgggaga taatcaaaca   1020
gctgttgtaa tagaaaacca tccaactgat agccgtgtga aactctcgga ggataataaa   1080
gtacagacgc tgacctctcg gatgggaact ggtggcggga atgtacccct tattatgaac   1140
actcctaaaa cgttaaaaat ccgctctggc tgtgaaggcg gtggtaaggg tgcattgata   1200
caagatgata agtctgcaac tcttggatgc aataatgatc agactgtttt tgtgcctacc   1260
gcatatggca tctgttctga taaaagcaat tccatgcagt caagcaatcc acatagcggt   1320
atatatgaag cagatacttc tcgaaccatt gatgctaatg gaggaaatcc aggatgtaat   1380
caaggtggta ttgcagtagt tgctctgcaa ggctcgatga ttggaagaga ggataaaaac   1440
ggtccccaag gaagcggtat agatgaagat gtttcttttta cgcttaatac cgctgatcgt   1500
catgctgttg cctatgccat gactaccgga gcctatgcac aggttgaaga agataaagca   1560
cctactctat tgtcgagaga ttataaggat gctcctgttg tgactcagcc ttcttacggt   1620
attgatcggg cggcttttaa tcaaggacag aacgctcttt ataaaccgac tatagatgaa   1680
gaacagcaac ctacgcttac agcaaaaggt cctggagcag tggcacaacc agcatcattt   1740
tatcctcaga tgaaagctga agtcaatgc tacagacagg acggtacatc aaatacgatt   1800
atcaatggca ccaatccagg ctatcaaaat ggattggttg aaccggacta tattgttcga   1860
aggcttacac caacggaatg tgcaagattg caaggcttcc ccgatgattg gtgtgatgac   1920
cttggtacgg aaaatcctac agaagatgaa atttcattct ggacggaggt ttgggaaacc   1980
caccgcaaaa ttataggtaa aagtaaaaag ccaaaaacaa gaaatcagat tataaaatgg   2040
cttaacaatc ctcattctga ttcagctgaa tacaaaatgt ggggtaatgg tgtagcactt   2100
ccatgcgttt gttttgtgct gactggcatt gtgttatcta cacaaaatac cgccgattaa   2160
```

<210> SEQ ID NO 7
<211> LENGTH: 1089
<212> TYPE: DNA
<213> ORGANISM: Artificial sequence
<220> FEATURE:
<223> OTHER INFORMATION: Synthetic polynucleotide

<400> SEQUENCE: 7

```
atgaactgta ttagtttttt tgcgggtgcg ggtggactgg atatggggat tcacaaagct     60
ggatttgacg tgcgagtttc tgtggaactt gaacctgtat actgtgaaac attgcggaca    120
aatcatccta attggaatgt ggtagagggt gatattatga cgtatacacc agagcaagta    180
ttggaacaag cggacttaca agaaggagaa gtcgatttga tgattggcgg cagcccatgt    240
caatcccttta gtacgcagg aaagcgtcaa gcattttcag atccacgcgg acaagcaatg    300
ttgaaatttg caaaacttgt tcgtgatatt cgaccaaaag cttttatgat agagaacgta    360
cgaggtttat tgtctgcggc tttaaagcat cgtccattaa gtgagagagg gaaagatgct    420
ttgccattta ctgaggaaga gcaaccagga agtgcattgg catatgtatt acaacaattt    480
gaggggtatg acattcaaga acctactcta ttaaatgcag cgaattatgg ggttcctcaa    540
aaacgtgaac gtgtatttat tataggagtt cgccaagact tagagaaaac atttgtattt    600
cctgaaccta cacataatga aaaaggaacg gatgggaaaa agccatgggt tacagtagga    660
gaagtgttaa aacagattga aacaaaggaa catcactatc agtcatattc tccagaacga    720
ttaaaatata tgaagatgat tccaacaggt ggtgggaatt ggcgtgacct tccagaagaa    780
```

| | |
|---|---|
| gtagtaaaag atgctatggg aggagcctat acaagtggag gaggaaaggt aggattcttc | 840 |
| cgccgattaa atatagataa gccatctcca acgttgttaa cgtcaccagc tcaaaagagt | 900 |
| accaacttag ggcatccatt tgaaaatcgt ccactgagca ttgaagagta cttagctatt | 960 |
| caagaatttc ctgaagatta tcatgtagcg ggtacactta tgaagcaata cactcaaatt | 1020 |
| ggaaatgcag tacctgtccg cttggcggag attttaggga atgccattcg agagacatta | 1080 |
| gaagcgtaa | 1089 |

```
<210> SEQ ID NO 8
<211> LENGTH: 1317
<212> TYPE: DNA
<213> ORGANISM: Artificial sequence
<220> FEATURE:
<223> OTHER INFORMATION: Synthetic polynucleotide

<400> SEQUENCE: 8
```

| | |
|---|---|
| atgtttaaag aagaattagc tattgagaaa atggaagatg aagtagtaat agaagttgaa | 60 |
| agcttaccaa tgtgtataga aaacggaaaa acttatgcaa taaaacaacc aaatcccaat | 120 |
| tcatatacac acggttattt caaatatcca tgtaaattta ttccagaaat accaagatgg | 180 |
| tttatgaata agtaccttgg ggagggaaag gcaagcgttt tagacccatt tagtggtagc | 240 |
| ggaactacat tattagaatc cattataaat ggacatgatg cttatggaac agaaatagat | 300 |
| aattttgcta agtattaat taaggttaag acgactcctt aaagttaca agaaatcaat | 360 |
| gaaataatcg attggctaga aagaataatt aaacaatatc aagaatctta tatggattat | 420 |
| aaaaatcctg tagttcctca aataaacaac ttgtatcact ggttttcaga gcaaaatgtt | 480 |
| caaaaactag gtcttattaa aaatgagata atgaattgg agaattcagc aataatagat | 540 |
| tttttaaatg tatgtttagc aagttcaatt aggaaatgtt cgaatgctga tgatgtgtct | 600 |
| cctaagccat atgtatcaag taaaattgaa aaagtacctt ctgatccctt tatcgtgttt | 660 |
| cctaatattg tgaataaata cttagcatat atgaaagaat ttttaaatta cactctaagt | 720 |
| aataagatag gaaaagtaga atattagag ggggatgctt taaacataaa ggcaaattca | 780 |
| aaaattgacg tagcaattac gtcgcctcct tatataaatg catttgacta tgctaggaca | 840 |
| ttaagattag aaaatttatg gctaggctta gactccgaag aaacaattaa ggataagaaa | 900 |
| aaatcttatg taggtactga aaatataact actaaaaaag taaatcaga attagatttg | 960 |
| tcaattttag aactaagtaa gcaacttaag gaagtatatt acgatattga aaaaattgat | 1020 |
| caaaagaggg cacttattgt taaaagtttt tttgaggata tgcataagaa cttaattgag | 1080 |
| gtttataatg tgttagcaga aggtggtaaa tattgtattg ttattgggaa tagcagtata | 1140 |
| aggaaaatta atgttgaaag ttggagcatt atttgtgata tagcgagagt gattggatttt | 1200 |
| gaaatcgata cttactttag ctatataatc aaaaatcact atttaagaat tcctagaggt | 1260 |
| aataagggtg ggaaaataaa taagattttt gtatttgttt taaaaaagtc tacttaa | 1317 |

```
<210> SEQ ID NO 9
<211> LENGTH: 1293
<212> TYPE: DNA
<213> ORGANISM: Artificial sequence
<220> FEATURE:
<223> OTHER INFORMATION: Synthetic polynucleotide

<400> SEQUENCE: 9
```

| | |
|---|---|
| atgatagatt ataatggtat tgaaaaaagc tttaatgtgc tttatccgga aattgaaaat | 60 |
| gcaacatatt taagtcaagt taattattca gatgaattaa aaaggcctta ccaacgttgg | 120 |

| | |
|---|---|
| tataggtata aagagggttt ttcagttgag cttgttaaaa gattaattaa agaacaagct | 180 |
| aagagatcaa caggaactat attagatcca ttttcaggta gcgggagcac attaattggt | 240 |
| gctaatgaat taggatataa aggactaggg tttgaggtta atccattttc ttactttta | 300 |
| agcaaagtta aactagaaaa ttatacttta ggcgaaatta cgcttttta gagcttgttt | 360 |
| gaacaggtgt taaatgaaga aaatggaata tttccgatgc caaatttatc ttttgctgat | 420 |
| aaggttttta ataagaagt acaggataaa cttatgtcga ttaaaaaaa tataattgac | 480 |
| cttgaaaatg aagggataaa tccaaatgtt gtaaatttat tgaaatttggg ttggttatct | 540 |
| tctatagaag aattatctaa ttatagaaaa gctggtaatg gattaaaaaa aagaaagtta | 600 |
| aagaatccaa tcgtactaaa taaagaggac gtttactata aactggatca tatttattcg | 660 |
| aatatgtata cagatcttga aacaaagaag ggtacgcgaa atatacaact tataaatcat | 720 |
| acatgtattg atatggataa atttattgaa gatagtagcg ttacaggtgt tatttttttct | 780 |
| ccaccttatg ctaattgctt cgactatact gaaatttata agttagagct gtggtttggg | 840 |
| ggctttgtag caaactatga ggaaatgaga actcttaaaa aatcttcact aaggtcacat | 900 |
| cttaatgcta atttaaaga agatatagat aatgtttata caattccatt attagaagat | 960 |
| atattaagta aattgaaaga aaagaaactg tgggataaaa agataccgat tatgttgaaa | 1020 |
| ttgtatttcc atgatatgtt tagagtgatt gaaaaatgct attcagcatt agaaccaggt | 1080 |
| ggttttttgta ctattgtagt aagtaattct tcttatggag gaattgtggt accaactgat | 1140 |
| ttattgttct caattttttgc ggaaaagata ggttttgaag taagtagaat tgaagttgca | 1200 |
| cgttatataa tcacaagctc tcaacaatat aatattacaa aggaacaaaa aaactttta | 1260 |
| agggaaagtg ttatatgttt aaagaagaat tag | 1293 |

<210> SEQ ID NO 10
<211> LENGTH: 1053
<212> TYPE: DNA
<213> ORGANISM: Artificial sequence
<220> FEATURE:
<223> OTHER INFORMATION: Synthetic polynucleotide

<400> SEQUENCE: 10

| | |
|---|---|
| atgatattta gattaggtga attattttgc ggcccaggtg ggatcgcttg gggtgcaatg | 60 |
| aatgctagta ttgaagatcc aaactttgcg attgtacatc agtgggcaaa tgactatgac | 120 |
| gcagatacct gtgaaacata tagattaaat atctgtcctg atactcctaa tactgtttac | 180 |
| catgcggata ttcgcaaatt cgatatgtct aaactagccc cgattgatgc attggcattt | 240 |
| ggtttcccat gcaatgacta tagtgttgtt ggtgagcaaa aaggtatgga cggggtattc | 300 |
| ggtcccttgt attcgtatgg tgtcaaagct ctaaaactgt ttaaacccaa gtggttttta | 360 |
| gcagaaaatg ttgaggact agaaatgca atgatggga aagccttcac taagattctc | 420 |
| aaggaactga gggaagctgg ctatacaatt acacctcatc tctacaaatt tgaggaatac | 480 |
| ggagtccctc aagcgaggca ccgtttgatt atcgttggca tacgggatga catcgatgtt | 540 |
| gaatttaaag tcccatcgac agcaccctat gtcggaatcg ataatacttg caaaaatgca | 600 |
| atagaaaatc cccctattcc agaggatgca tataataatg aattgacaag acaatccgaa | 660 |
| actgttgtta gaaggttgca gcatattcta cctggacaaa atgcatttac ggcagacctt | 720 |
| ccagaagatt tgcgacttaa tattagagga gcaaaaataa gtcaaatata taagaggctc | 780 |
| gatccaacta agccttccta tacggttacg ggaagcggtg gtggaggaac acatatttac | 840 |

```
cattgggaag aaccacgagc attgactaac agagagcggg caagattaca gactttccct    900
gatacttata gattcgtagg aagtaaagag agtgtacgca aacaaattgg aatggcagta    960
ccttgtcagg gtgcaaaaat cattttgag gcaatattga agtgttttgc tggaattgaa   1020
tatgagagcg tagagccaag tattaaagaa tga                                1053
```

<210> SEQ ID NO 11
<211> LENGTH: 1242
<212> TYPE: DNA
<213> ORGANISM: Artificial sequence
<220> FEATURE:
<223> OTHER INFORMATION: Synthetic polynucleotide

<400> SEQUENCE: 11

```
atgttgatag agaagattaa aacgaaacaa ctcatccccg ctgaatataa cccaaggaaa     60
gatttaaaac cgggtgattc ggaatatgag aaacttaaac gctcccttga ggagtttggt    120
tatgtagaac ccgttatatg gaataagact acaggcagag ttatcggagg tcatcagcgt    180
ttaaaagtcc tgcttagtat gggtatagat gagatagaat gcgtagtagt tgaaatggat    240
gagcaaaagg agaaggcgct gaacattgca ctaaataaaa ttagtggtga ttgggataaa    300
gacaaattag cacttctcat cacggaccta atgcttcag actttgatgt gtctttgaca    360
ggttttgacc cggagagtt ggacgatctt ttcaaggatt cccttaagga taatataaaa    420
gaagatgatt ttgatgtaga cagcgagctg aaaaagcccg ctgtttcgca tttaggggat    480
atttggctac ttggacagca tcgattagtc tgtggagaca gtacaaagaa agacaccttt    540
gatgtcttga tggatgggaa agctgccaat ctggtagtta cggaccctcc atataacgtc    600
aactatgaag gcactgctgg aaaaatcaaa aatgacaata tggctaatga agcgttctat    660
gattttctgc ttgcggcatt tcaaaacacc gaagcagcga tggcaaagga cgcatctatt    720
tatgtatttc atgctgatac ggaaggactc aattttagaa gagcattctc cgatgcagga    780
ttttatcttt ccggtacttg tatatggaaa aagcagtccc ttgttctcgg tcgctcccca    840
tatcagtggc agcatgaacc agtactcttt ggatggaaaa agaaaggcaa gcatctctgg    900
tattcagacc gcaagcagac aaccatctgg gagtttgaga aaccaaagaa aaacggcgac    960
catccaacca tgaaaccagt ggcacttgtg gcttatccca ttatgaactc aagccttagt   1020
aactgcatcg tgctcgatcc tttcggtggt tcaggaagta cactgattgc ctgtgagcaa   1080
acagatagaa tctgctacac cattgaactg gatgaaaagt actgcgatgt tatttgtgaaa   1140 agatatattg agcaagtggg aaactctgat ggtgtatttc tattaagaga tcgcttgaaa   1200
ttcagatatt gtgacctgcc agaggtgaat gaggatgagt aa                     1242
```

<210> SEQ ID NO 12
<211> LENGTH: 648
<212> TYPE: DNA
<213> ORGANISM: Artificial sequence
<220> FEATURE:
<223> OTHER INFORMATION: Synthetic polynucleotide

<400> SEQUENCE: 12

```
atgacattct caaccaacca gcttcgcaat tccattcaac gcggcgattg catcgaagtg     60
atgcaggcca tcccttcccg gtccgtcgat tttatcctga ccgacccgcc ctatctcgtc    120
cgctacaaat gccgcgacgg tcgctcaatc atgaacgacg acaacgccga gtggctggag    180
ccggccgcgc acgagatgta tcgggttttg aaccgcgaca gcctctgcgt cagcttctat    240
ggctggacgc agaccgaccg cttcatcgcg gcctggcgtt ccgcaggatt ccggatcgtc    300
```

| | |
|---|---|
| gggcacatcg tctttcgcaa acgctatgcc tcagcaaagc ggttcgtcag ctacacgcac | 360 |
| gaatccgctt acgtgctggc aagggccgt ccggcgctgc cggagcatcc gccagccgat | 420 |
| gtgatcgact tcccctatag cggcaaccgg ctgcatccga cccagaagcc ggtgatggcg | 480 |
| ctcatgccgc tgattacagc tttctgcccg aaggcgggt tggtgctcga cccttctgt | 540 |
| ggctccggct cgaccctggt cgcggcccgg caagccggtt gcgattatct cggcatcgaa | 600 |
| ctggaccacc gctatcaccg gatcgccgcc cggagacttg cggcataa | 648 |

<210> SEQ ID NO 13
<211> LENGTH: 1983
<212> TYPE: DNA
<213> ORGANISM: Artificial sequence
<220> FEATURE:
<223> OTHER INFORMATION: Synthetic polynucleotide

<400> SEQUENCE: 13

| | |
|---|---|
| atgcacggaa tcgaaaagct caacctgaac gacccggaaa cccaaagcgc cgatgtggtc | 60 |
| gccgagaata tcgatgccct gcgctcgctg tttccggaag cgttcgagga agggaagatt | 120 |
| gatttcgagg tgctgaagca attgctcggc ggcgcggttg acgagcgcga cgagaaatac | 180 |
| ggactgaact ggcacggcaa gcgcaaggca cggcagatcg cgctgacgcc gtccaccggc | 240 |
| acgctgttac cgtgtcccga cgaaagtgtc gattgggata cgacgcagaa cttagtgata | 300 |
| gagggcgaca acctcgaagt cctgaagctt ctacaaaaga gctacgccgg caaggtgaag | 360 |
| ctcatctaca tcgacccgcc atacaatacc gggaaggaat ttatttaccc cgaccgcttt | 420 |
| caggacaacc tggacaccta cttaaaatac acaggtcaaa aaggggagga tggccttaag | 480 |
| actacgagca cactgaaaaa tgacggcagg tttcatacga actggctgaa tatgatatat | 540 |
| cctcgcttaa agcttgcgag acaatgctc gctgacgacg gggcgatatt catttccatc | 600 |
| gatgataacg aaaaggccaa tcttaaagag atatgtgatg aaatatttgg tgaagataat | 660 |
| tttctcacgg cgataattgt ccaatctaac aagcgtggac aaacatacaa agagatagcg | 720 |
| aagtgtcatg aatatatcct tgtctattac aaaacagaga acggcgctct cggcgaactc | 780 |
| gataaggatg gcgatgccct cccttatgct gacgaacatg gcggatacga tctttgggaa | 840 |
| ctacggaatc gaaatccaaa attcggacgc acaaccggc caaatctgta ttttccaatc | 900 |
| tacgtgaatc taactctgt cggggctaat ggcttgcaa gcattagctt gacgaaaagc | 960 |
| gacgaatact gtcgggaggc attgccaaag aacagcgagg gcgcggacag ttgctggaga | 1020 |
| tggagttcaa agaaagttca aactgatggc atagatgcta ctccgatcac tgttttttgcc | 1080 |
| aaacagagac gagacggcga atggaacatt tacgagaagt cccgcaagag cacgaccaaa | 1140 |
| gccaaaagta tttggagcga tactgctgtt ataagtgagc agggaacggt tgaggccgga | 1200 |
| aaattaggga tgagcggggt tctcgatttt ccgaagccaa tagaactcat ccggcgttgc | 1260 |
| gtatttcttg gcacaaacga agatgatctt gtgatgact tttttgccgg atcgggaacc | 1320 |
| accgcccacg ctgtgatgct ccaatcggct caagatggtt tgtctagaag atggatatcg | 1380 |
| gtgcagcttc cagaaccgac atatgagtac aaggatgggg agaaggttgc gaaaccgcaa | 1440 |
| aataaaatcg cttttgaaaa tggacacgaa acgatcgccg atatttgcaa ggaacggatt | 1500 |
| cgtcgctcgg caaacaaatt gaaagaggaa tatccgggaa ataatgccga tcttggtttc | 1560 |
| agggtctttta agctcgcgca gtcaaatatc cgcgcgtggg aaccggagcc gtccgacatt | 1620 |
| gaaggtacgc tccttgccaa cgcagaacac ctcgcacaag gtcgctccga acaagacgtt | 1680 |

| ctccatgagc tattgctcaa gcttggtctc gacctctgcg tcccaatcga gaagaagcag | 1740 |
| atcgccggga agccgtcca ttccatcggc ggcggcgcgc tgatcgtctg cctcgctgac | 1800 |
| ggactgacca aggacgtggt ggaggcgctt gccaacggca ttgtcgcgtg cgcaaggca | 1860 |
| ctcgccccgg ccgtcgatac ccgtgtcgtg ttcaaggatt ccggctttgc cgacgacgtg | 1920 |
| gccaagacca acatggccgc cattctgaat cagaacggca ttctcgacgt gcgtagtctc | 1980 |
| tga | 1983 |

<210> SEQ ID NO 14
<211> LENGTH: 1311
<212> TYPE: DNA
<213> ORGANISM: Artificial sequence
<220> FEATURE:
<223> OTHER INFORMATION: Synthetic polynucleotide

<400> SEQUENCE: 14

| atgcataaca tccaatgcat cgctgtcggc tctcttaagc cgaaccctcg taacgtccgc | 60 |
| acgcactcga aaaggcaaat cagccaaatc gcaaatagca tttcgcgatt tggctggacc | 120 |
| tatccgctat tggttgatga aacctcatt actctggcag gcatggtcg cctacttgcc | 180 |
| gcccggcaac ttggcttaga aagattccg gtaatcgtct tcggcggtct cagcgatacc | 240 |
| gaaaagcggg ccttgatgtt ggcggacaat aaaatcgccg ccaacgccgg atgggaccgc | 300 |
| aaaatcctcg ccaaggagct tggcgaactc tccgatcttc ttcctgagat aaatctcgat | 360 |
| atcgaaataa ccggatttc cgcggctgag atcgaacctt gctcgtcga tctggtcgac | 420 |
| ggagaatgcg atccagcaga tgacgctccc ctgctggcga aggaggccat cactcgcaag | 480 |
| ggtgatctct ggacattagg cgaccacaga ctcatttgtg cagatgcctg cagtcgcaag | 540 |
| gcataccaag cgctcatgaa agattgtttc gcgtcggtcg ctatacccga tcaaccctac | 600 |
| aacgattcca tcgtcaagat cgtcgggcga gggaagatca agcatcggga attcgcccgc | 660 |
| gcatccggcg aactctcgcc cgagcaattt gtgaacttcc aacgacaatg gatggagctc | 720 |
| tgttcagagt tttcaaagcc tggttcaatc catttcgtct ttatagattg gcgccatctc | 780 |
| tcggaggccc tgactgcggg gcacgctgtc tacagcgagc tcaagaatgt cgccgtctgg | 840 |
| tgcaagacca atgccgggca aggtagcttc tatcgctcac aacatgagct catccttgtt | 900 |
| tttaaaaacg gtgatgcccc acaccagaat aacatcgaat taggtcgcca cggccgcaat | 960 |
| cgttcaaacg tctggacgta cgccggcgta aacacattcc gcgctggccg gatggatgat | 1020 |
| ttgtctgtcc atccgaccgt taagccggtc ggactggtcc tggatgcaat caaggattgt | 1080 |
| tcgcgtcgcg gggacattgt cctcgatccc tttatgggat ccggaacaac aatccttgct | 1140 |
| gccgaacggg ttgaccgacg cggcttcggc atcgagatcg acccgctcta tgtcgacgtc | 1200 |
| gcgattcgtc gttggcagca atttactggg caggatgcga tcctcgaagc cagcggctta | 1260 |
| acattccacg agattgaggc aaaacgatct accgatggag gtggcaaatg a | 1311 |

<210> SEQ ID NO 15
<211> LENGTH: 1131
<212> TYPE: DNA
<213> ORGANISM: Artificial sequence
<220> FEATURE:
<223> OTHER INFORMATION: Synthetic polynucleotide

<400> SEQUENCE: 15

| atgggtgtgt cgcgtcgcgg ggcgtctgca agggcgcccc gcaccaaatt tgactctccc | 60 |
| gcttcgcgca tcatcgttgg cgactgcgtc gccgcgatgt cgaagcttcc atccggatca | 120 |

```
gccgatctgg tcttcgcgga tccaccctac aatctgcaac tcaagggcga tctcaagcgt       180
cccgacgaat cgcacgtcga tgccgtcaac gacgactggg acaagttctc gtccttcgca       240
gcgtacgacg atttcacccg cgcctggctg ctcgcctgcc gccgcgtcat gaagccgacg       300
gccaccatct gggtgatcgg atcgtatcac aacatcttcc gggtcggcgc gatcatgcag       360
gacctcggct tctgggtcct caacgacatc gtctggcgca agaccaaccc gatgccgaat       420
ttccgcggcc gtcgcttcac caatgcccac gaaaccatga tctgggccgc gcgcgacgag       480
aacgccaagg gctacacgtt caactacgag gcgttgaagg cctccaacga ggacgtgcag       540
gcgcgatcgg actggctgat tccgctctgc accggcaacg aacggctgaa ggacaaagac       600
ggcaggaaag ttcatccgac ccagaagccc gagggcctgc tggcgcgggt gctgctgtcg       660
tcgtcaaggc ccggcgatct catcatcgat ccgttcaacg gcaccggcac caccggagcg       720
gtcgccaagc gtctcggccg caactatatc ggcttcgagc gcgatcagac ctacgccgcc       780
gccgccgaga aacgcatcgc ggccatcgaa ccgctgccgg aagccaccat cgccccgttc       840
atgaccgcgc gcgaagcgcc gcgcgtggcg ttctccgaac tgatcgagcg cggcatgatc       900
tcgcccggtg cgaaactcgt cgacgcaaag aagcgtcatg gcgcgttggt gcgcgccgac       960
ggcgccatca tgctcggcga caaggtcgga tcgattcacc gcatcggcgc ggtggcgcaa       1020
ggtgcgggcg cctgcaacgg ctggaccttc tggcacatcg aaaccagcaa gggcctcagg      1080
ctgatcgacg agttgcgcgc cgaaatccgc agcgagatgg cggccggctg a               1131
```